(12) United States Patent
Feng et al.

(10) Patent No.: US 10,364,472 B2
(45) Date of Patent: Jul. 30, 2019

(54) METHOD FOR IDENTIFYING WUZHISHAN MINIATURE PIG INBRED LINE BY USING 145 SNPS

(71) Applicant: GRAND LIFE SCIENCE & TECHNOLOGY, LTD., Beijing (CN)

(72) Inventors: Shutang Feng, Beijing (CN); Yulian Mu, Beijing (CN); Jianlin Han, Beijing (CN); Kui Li, Beijing (CN); Qian Gao, Beijing (CN)

(73) Assignee: GRAND LIFE SCIENCE & TECHNOLOGY, LTD., Beijing (CN)

( * ) Notice: Subject to any disclaimer, the term of this patent is extended or adjusted under 35 U.S.C. 154(b) by 44 days.

(21) Appl. No.: 15/521,262

(22) PCT Filed: Oct. 21, 2014

(86) PCT No.: PCT/CN2014/000937
§ 371 (c)(1),
(2) Date: Apr. 21, 2017

(87) PCT Pub. No.: WO2016/061711
PCT Pub. Date: Apr. 28, 2016

(65) Prior Publication Data
US 2017/0327903 A1 Nov. 16, 2017

(51) Int. Cl.
| | | |
|---|---|---|
| *C12Q 1/68* | (2018.01) | |
| *C12Q 1/6888* | (2018.01) | |
| *A01K 67/027* | (2006.01) | |
| *C12N 15/11* | (2006.01) | |
| *A01K 67/00* | (2006.01) | |
| *C12N 15/00* | (2006.01) | |

(52) U.S. Cl.
CPC .......... *C12Q 1/6888* (2013.01); *A01K 67/027* (2013.01); *C12N 15/11* (2013.01); *A01K 67/00* (2013.01); *A01K 2227/108* (2013.01); *C12N 15/00* (2013.01); *C12Q 2600/156* (2013.01)

(58) Field of Classification Search
None
See application file for complete search history.

(56) References Cited

FOREIGN PATENT DOCUMENTS

| | | | |
|---|---|---|---|
| CN | 103923993 | A | 7/2014 |
| CN | 103923994 | A | 7/2014 |
| CN | 104293963 | A | 1/2015 |

OTHER PUBLICATIONS

ISA State Intellectual Property Office of the People's Republic of China, International Search Report Issued in Application No. PCT/CN2014/000937, dated Jul. 27, 2015, WIPO, 4 pages.

*Primary Examiner* — James Martinell
(74) *Attorney, Agent, or Firm* — McCoy Russell LLP

(57) ABSTRACT

The present invention discloses a method for identifying Wuzhishan miniature pig inbred line by using 145 SNPs. The method for auxiliarily identifying whether a pig to be tested is Wuzhishan miniature pig inbred line, provided by the present invention, comprises the following steps: testing genotypes based on 145 SNP sites of the pig to be tested; if all standards of (1) to (145) are satisfied, the pig to be tested is a candidate for Wuzhishan miniature pig inbred line; if all the standards of the above (1) to (145) are not satisfied, the pig to be tested is a candidate for non-Wuzhishan miniature pig inbred line.

14 Claims, No Drawings
Specification includes a Sequence Listing.

SEQUENCE LISTING

```
<160> NUMBER OF SEQ ID NOS: 145

<210> SEQ ID NO 1
<211> LENGTH: 50
<212> TYPE: DNA
<213> ORGANISM: Sus scrofa
<220> FEATURE:
<223> OTHER INFORMATION: M1GA0025062

<400> SEQUENCE: 1
tttggtctac agaacgagag tctcgcgtcg gggtctgagc atcttgcgtg            50

<210> SEQ ID NO 2
<211> LENGTH: 50
<212> TYPE: DNA
<213> ORGANISM: Sus scrofa
<220> FEATURE:
<223> OTHER INFORMATION: DRGA0017627

<400> SEQUENCE: 2
tctgatacaa acaaattccg acttgtggaa ttgtaaatat ttgtcgattc            50
```

```
<210> SEQ ID NO 3
<211> LENGTH: 50
<212> TYPE: DNA
<213> ORGANISM: Sus scrofa
<220> FEATURE:
<223> OTHER INFORMATION: H3GA0056137

<400> SEQUENCE: 3
tggtgttggc tgcgcgtggg agggaggtat cttagaagca aacgggataa         50

<210> SEQ ID NO 4
<211> LENGTH: 50
<212> TYPE: DNA
<213> ORGANISM: Sus scrofa
<220> FEATURE:
<223> OTHER INFORMATION: MARC0039661

<400> SEQUENCE: 4 accagggac aaaggaaacc tgtttcctac cgttccatta cgtcagtgtg          50

<210> SEQ ID NO 5
<211> LENGTH: 50
<212> TYPE: DNA
<213> ORGANISM: Sus scrofa
<220> FEATURE:
<223> OTHER INFORMATION: ASGA0085025

<400> SEQUENCE: 5
acaacaaaaa agaaagcagg ccaaaaaaga gttcacactc tacaaggcca         50

<210> SEQ ID NO 6
<211> LENGTH: 50
<212> TYPE: DNA
<213> ORGANISM: Sus scrofa
<220> FEATURE:
<223> OTHER INFORMATION: ASGA0098570

<400> SEQUENCE: 6
cgaatcgaag aaaatacaga ctctctgtag ttccagcacc aaaggagaag         50

<210> SEQ ID NO 7
<211> LENGTH: 50
<212> TYPE: DNA
<213> ORGANISM: Sus scrofa
<220> FEATURE:
<223> OTHER INFORMATION: MARC0063358

<400> SEQUENCE: 7
ctgctttact cagtccttct tgtgtcgcgt ctgtcatcgt tgtgtagctc         50

<210> SEQ ID NO 8
<211> LENGTH: 50
<212> TYPE: DNA
<213> ORGANISM: Sus scrofa
<220> FEATURE:
<223> OTHER INFORMATION: ASGA0085437

<400> SEQUENCE: 8
tcgtcgtaag actgtcgcaa gactgtcgca gtgtcgcagt gacagcaccc         50

<210> SEQ ID NO 9
<211> LENGTH: 50
<212> TYPE: DNA
<213> ORGANISM: Sus scrofa
<220> FEATURE:
<223> OTHER INFORMATION: MARC0096709
```

<400> SEQUENCE: 9
cccactgagc agacaaatca gccttaaaca ctgctgacct taaacatcag        50

<210> SEQ ID NO 10
<211> LENGTH: 50
<212> TYPE: DNA
<213> ORGANISM: Sus scrofa
<220> FEATURE:
<223> OTHER INFORMATION: H3GA0052387

<400> SEQUENCE: 10
gggtccccag cagcgtcttt ttatttgtat tagtggtgtc tgccaacaag        50

<210> SEQ ID NO 11
<211> LENGTH: 50
<212> TYPE: DNA
<213> ORGANISM: Sus scrofa
<220> FEATURE:
<223> OTHER INFORMATION: ASGA0000264

<400> SEQUENCE: 11
ggctggagga acatggattt ggaagcagaa gctcggatgg agatgcagag        50

<210> SEQ ID NO 12
<211> LENGTH: 50
<212> TYPE: DNA
<213> ORGANISM: Sus scrofa
<220> FEATURE:
<223> OTHER INFORMATION: ALGA0000195

<400> SEQUENCE: 12
ctcttccagg taagattcat ttacaccgaa tccattttcc gcagcttagc        50

<210> SEQ ID NO 13
<211> LENGTH: 50
<212> TYPE: DNA
<213> ORGANISM: Sus scrofa
<220> FEATURE:
<223> OTHER INFORMATION: H3GA0001444

<400> SEQUENCE: 13
ggtatccctt taatataggc gttcctaacc tggatgtttt tgagttgaac        50

<210> SEQ ID NO 14
<211> LENGTH: 50
<212> TYPE: DNA
<213> ORGANISM: Sus scrofa
<220> FEATURE:
<223> OTHER INFORMATION: ASGA0002293

<400> SEQUENCE: 14
ggccatgcct gcagcatatg gaagttcttg gaccaggtat tgagatctga        50

<210> SEQ ID NO 15
<211> LENGTH: 50
<212> TYPE: DNA
<213> ORGANISM: Sus scrofa
<220> FEATURE:
<223> OTHER INFORMATION: INRA0001752

<400> SEQUENCE: 15
taggtagata gatagacaga tagttagata gcagacaata gatacagaaa        50

<210> SEQ ID NO 16

<211> LENGTH: 50
<212> TYPE: DNA
<213> ORGANISM: Sus scrofa
<220> FEATURE:
<223> OTHER INFORMATION: H3GA0001445

<400> SEQUENCE: 16
tgggaataca caaagaatt aaatcaacac ctttcacaat cacaggccaa         50

<210> SEQ ID NO 17
<211> LENGTH: 50
<212> TYPE: DNA
<213> ORGANISM: Sus scrofa
<220> FEATURE:
<223> OTHER INFORMATION: ALGA0002595

<400> SEQUENCE: 17
tcaagaagaa tttctagctg agatgaaaag agttctcctc caaagtaaaa         50

<210> SEQ ID NO 18
<211> LENGTH: 50
<212> TYPE: DNA
<213> ORGANISM: Sus scrofa
<220> FEATURE:
<223> OTHER INFORMATION: ALGA0002600

<400> SEQUENCE: 18
gatatacagt aggaaagata tgtcagctcc ctctccctca cataactaac         50

<210> SEQ ID NO 19
<211> LENGTH: 50
<212> TYPE: DNA
<213> ORGANISM: Sus scrofa
<220> FEATURE:
<223> OTHER INFORMATION: DRGA0000563

<400> SEQUENCE: 19
gattctgaac ttgaaactct cacttcttcc taagataagc aaactacatg         50

<210> SEQ ID NO 20
<211> LENGTH: 50
<212> TYPE: DNA
<213> ORGANISM: Sus scrofa
<220> FEATURE:
<223> OTHER INFORMATION: DRGA0000565

<400> SEQUENCE: 20
ggagtcatat gtctatcagt aaagagtcag ctaatacttt aaactttgcc         50

<210> SEQ ID NO 21
<211> LENGTH: 50
<212> TYPE: DNA
<213> ORGANISM: Sus scrofa
<220> FEATURE:
<223> OTHER INFORMATION: INRA0001761

<400> SEQUENCE: 21
ttctggcaca aatgtgctac ttttatatct ttttcccatt ttaaaacttt         50

<210> SEQ ID NO 22
<211> LENGTH: 50
<212> TYPE: DNA
<213> ORGANISM: Sus scrofa
<220> FEATURE:
<223> OTHER INFORMATION: MARC0104045

<400> SEQUENCE: 22

```
gagccacaat ggtaactcct cttatagcaa ttttaaata ccatgaaaat              50
```

```
<210> SEQ ID NO 23
<211> LENGTH: 50
<212> TYPE: DNA
<213> ORGANISM: Sus scrofa
<220> FEATURE:
<223> OTHER INFORMATION: ALGA0002601

<400> SEQUENCE: 23
cttccttttt cctttcaag agctttgctg cccaagacag gaatccagag              50
```

```
<210> SEQ ID NO 24
<211> LENGTH: 50
<212> TYPE: DNA
<213> ORGANISM: Sus scrofa
<220> FEATURE:
<223> OTHER INFORMATION: DRGA0000569

<400> SEQUENCE: 24
ttggtctttt ttgtagcctt ccttttttct gccttttaaa tactgtggtg              50
```

```
<210> SEQ ID NO 25
<211> LENGTH: 50
<212> TYPE: DNA
<213> ORGANISM: Sus scrofa
<220> FEATURE:
<223> OTHER INFORMATION: ALGA0002608

<400> SEQUENCE: 25
aggggaagac atggttgtgg cttgaccttg gaaagatgag ctaaaggtgc              50
```

```
<210> SEQ ID NO 26
<211> LENGTH: 50
<212> TYPE: DNA
<213> ORGANISM: Sus scrofa
<220> FEATURE:
<223> OTHER INFORMATION: DRGA0000568

<400> SEQUENCE: 26
atcacataca tactgaaaag tgatggaaca tatcttgaaa ccaatttgac              50
```

```
<210> SEQ ID NO 27
<211> LENGTH: 50
<212> TYPE: DNA
<213> ORGANISM: Sus scrofa
<220> FEATURE:
<223> OTHER INFORMATION: ALGA0002604

<400> SEQUENCE: 27
cagtaaagtg cttcagagct ttggtaattt gggcatcctt gtatcacctt              50
```

```
<210> SEQ ID NO 28
<211> LENGTH: 50
<212> TYPE: DNA
<213> ORGANISM: Sus scrofa
<220> FEATURE:
<223> OTHER INFORMATION: MARC0048118

<400> SEQUENCE: 28
caatggaggt aataagaaat ggttagttct atatgtactt tgagtgcaaa              50
```

```
<210> SEQ ID NO 29
<211> LENGTH: 50
<212> TYPE: DNA
```

```
<213> ORGANISM: Sus scrofa
<220> FEATURE:
<223> OTHER INFORMATION: ASGA0004229

<400> SEQUENCE: 29
aaggcacttc atagttaata gctattagaa tcctagagct gcatagagaa          50

<210> SEQ ID NO 30
<211> LENGTH: 50
<212> TYPE: DNA
<213> ORGANISM: Sus scrofa
<220> FEATURE:
<223> OTHER INFORMATION: MARC0007088

<400> SEQUENCE: 30
aacagtccac cagacaagcc tctgaaagcc cagggcacag ccaccactgt          50

<210> SEQ ID NO 31
<211> LENGTH: 50
<212> TYPE: DNA
<213> ORGANISM: Sus scrofa
<220> FEATURE:
<223> OTHER INFORMATION: MARC0000061

<400> SEQUENCE: 31
aagacgtgat gcagcaagct ctgtgatgta acaggtaccc cactctgctg          50

<210> SEQ ID NO 32
<211> LENGTH: 50
<212> TYPE: DNA
<213> ORGANISM: Sus scrofa
<220> FEATURE:
<223> OTHER INFORMATION: MARC0094747

<400> SEQUENCE: 32
ttcagatctc agtctggaca gggcagtgtg ttcttttat gataatgggc           50

<210> SEQ ID NO 33
<211> LENGTH: 50
<212> TYPE: DNA
<213> ORGANISM: Sus scrofa
<220> FEATURE:
<223> OTHER INFORMATION: MARC0007969

<400> SEQUENCE: 33
ctgaggatgg ttttatgcca agagactcca cagtcagctt aataacctta          50

<210> SEQ ID NO 34
<211> LENGTH: 50
<212> TYPE: DNA
<213> ORGANISM: Sus scrofa
<220> FEATURE:
<223> OTHER INFORMATION: ASGA0106092

<400> SEQUENCE: 34
aaatggttct gacccaaaag agaggactgt tctaagcaac catgtgcagg          50

<210> SEQ ID NO 35
<211> LENGTH: 50
<212> TYPE: DNA
<213> ORGANISM: Sus scrofa
<220> FEATURE:
<223> OTHER INFORMATION: ALGA0119806

<400> SEQUENCE: 35
tggacttccc aatgcctgcc ttgtctctcc tatcccagaa tccctcagtg          50
```

<210> SEQ ID NO 36
<211> LENGTH: 50
<212> TYPE: DNA
<213> ORGANISM: Sus scrofa
<220> FEATURE:
<223> OTHER INFORMATION: INRA0003745

<400> SEQUENCE: 36
actgcagcaa taagtgcaac tgtcactttg ttctgtggaa aatgccctgg         50

<210> SEQ ID NO 37
<211> LENGTH: 50
<212> TYPE: DNA
<213> ORGANISM: Sus scrofa
<220> FEATURE:
<223> OTHER INFORMATION: INRA0003746

<400> SEQUENCE: 37
catttgttct ttggggaaaa gattggacag aagagatcca tgttttctcc         50

<210> SEQ ID NO 38
<211> LENGTH: 50
<212> TYPE: DNA
<213> ORGANISM: Sus scrofa
<220> FEATURE:
<223> OTHER INFORMATION: ALGA0005490

<400> SEQUENCE: 38
tctcttgcac aaggggatat tctattgaat taatggccct ggaaggacaa         50

<210> SEQ ID NO 39
<211> LENGTH: 50
<212> TYPE: DNA
<213> ORGANISM: Sus scrofa
<220> FEATURE:
<223> OTHER INFORMATION: H3GA0002538

<400> SEQUENCE: 39
cacattaagc cttatgtttt acttacctcg gaagcatgag ccatgtgata         50

<210> SEQ ID NO 40
<211> LENGTH: 50
<212> TYPE: DNA
<213> ORGANISM: Sus scrofa
<220> FEATURE:
<223> OTHER INFORMATION: INRA0003749

<400> SEQUENCE: 40
atctgaatac agccaacgtt cagtgatacc acaccatcca ctttggacat         50

<210> SEQ ID NO 41
<211> LENGTH: 50
<212> TYPE: DNA
<213> ORGANISM: Sus scrofa
<220> FEATURE:
<223> OTHER INFORMATION: H3GA0002539

<400> SEQUENCE: 41
atcaatttgt accacgagtg agttggaatg actggcatta ggattcgaca         50

<210> SEQ ID NO 42
<211> LENGTH: 50
<212> TYPE: DNA
<213> ORGANISM: Sus scrofa
<220> FEATURE:

<223> OTHER INFORMATION: M1GA0001099

<400> SEQUENCE: 42
aaactcacca gggcaacatc ttccatgaag ctcatgtaac tttaatgcct                50

<210> SEQ ID NO 43
<211> LENGTH: 50
<212> TYPE: DNA
<213> ORGANISM: Sus scrofa
<220> FEATURE:
<223> OTHER INFORMATION: MARC0111831

<400> SEQUENCE: 43
aaataccttc ccgttctccc atttctaata taagacaggg atgaggatac                50

<210> SEQ ID NO 44
<211> LENGTH: 50
<212> TYPE: DNA
<213> ORGANISM: Sus scrofa
<220> FEATURE:
<223> OTHER INFORMATION: ASGA0005566

<400> SEQUENCE: 44
aatatgactg agttaggtac ttggagggtg aaggataaaa aagatacaga                50

<210> SEQ ID NO 45
<211> LENGTH: 50
<212> TYPE: DNA
<213> ORGANISM: Sus scrofa
<220> FEATURE:
<223> OTHER INFORMATION: ALGA0007578

<400> SEQUENCE: 45
cttgggtgct cttgaaaatc ccaattcaat tcaaacccag ctgttctgat                50

<210> SEQ ID NO 46
<211> LENGTH: 50
<212> TYPE: DNA
<213> ORGANISM: Sus scrofa
<220> FEATURE:
<223> OTHER INFORMATION: ASGA0005568

<400> SEQUENCE: 46
tgatctggca tttgaggact gttgtatcag tttgaaagta agacagcttg                50

<210> SEQ ID NO 47
<211> LENGTH: 50
<212> TYPE: DNA
<213> ORGANISM: Sus scrofa
<220> FEATURE:
<223> OTHER INFORMATION: INRA0005765

<400> SEQUENCE: 47
ccctccccct atatatattt aaaatataga tgttgcttaa tatcagaaca                50

<210> SEQ ID NO 48
<211> LENGTH: 50
<212> TYPE: DNA
<213> ORGANISM: Sus scrofa
<220> FEATURE:
<223> OTHER INFORMATION: MARC0095347

<400> SEQUENCE: 48
tagagtttgt gccaatctgg ttgtgccaca gcagggactc cctgtacaca                50

-continued

<210> SEQ ID NO 49
<211> LENGTH: 50
<212> TYPE: DNA
<213> ORGANISM: Sus scrofa
<220> FEATURE:
<223> OTHER INFORMATION: MARC0039015

<400> SEQUENCE: 49
tgactaaata aggtttgttc caaatattac agggcataat gaaaaagatc          50

<210> SEQ ID NO 50
<211> LENGTH: 50
<212> TYPE: DNA
<213> ORGANISM: Sus scrofa
<220> FEATURE:
<223> OTHER INFORMATION: DRGA0001892

<400> SEQUENCE: 50
ttaagtactt gccaaagaat taaaataaag ataagcaatg ctttaaaaaa          50

<210> SEQ ID NO 51
<211> LENGTH: 50
<212> TYPE: DNA
<213> ORGANISM: Sus scrofa
<220> FEATURE:
<223> OTHER INFORMATION: ALGA0007580

<400> SEQUENCE: 51
gctcattcat ccaacacata cacacaggct aatcagaagc aaacacccac          50

<210> SEQ ID NO 52
<211> LENGTH: 50
<212> TYPE: DNA
<213> ORGANISM: Sus scrofa
<220> FEATURE:
<223> OTHER INFORMATION: ALGA0007583

<400> SEQUENCE: 52
aggaaaattc cctgcctaaa gccacatagc atcatcttag gaaataaacc          50

<210> SEQ ID NO 53
<211> LENGTH: 50
<212> TYPE: DNA
<213> ORGANISM: Sus scrofa
<220> FEATURE:
<223> OTHER INFORMATION: MARC0095915

<400> SEQUENCE: 53
gctacagatg tatacgtaga ttcttataac tgtccaatga actaagtgtc          50

<210> SEQ ID NO 54
<211> LENGTH: 50
<212> TYPE: DNA
<213> ORGANISM: Sus scrofa
<220> FEATURE:
<223> OTHER INFORMATION: ASGA0005571

<400> SEQUENCE: 54
ccatgtagtt ttcagtccac tgtgaaattt taaccttttt cgtatgtcta          50

<210> SEQ ID NO 55
<211> LENGTH: 50
<212> TYPE: DNA
<213> ORGANISM: Sus scrofa
<220> FEATURE:
<223> OTHER INFORMATION: MARC0014134

<400> SEQUENCE: 55
caatcatttc ataccagt gtgcaaatat aatatgcaag accaaaaaaa         50

<210> SEQ ID NO 56
<211> LENGTH: 50
<212> TYPE: DNA
<213> ORGANISM: Sus scrofa
<220> FEATURE:
<223> OTHER INFORMATION: MARC0024233

<400> SEQUENCE: 56
aacctgtttc actcttgtcg atgcagccaa gtggcaggga agtcctcagc         50

<210> SEQ ID NO 57
<211> LENGTH: 50
<212> TYPE: DNA
<213> ORGANISM: Sus scrofa
<220> FEATURE:
<223> OTHER INFORMATION: H3GA0003548

<400> SEQUENCE: 57
agcttaacag gtggctctgg aggaaacaca cttggtctga gatatcacgg         50

<210> SEQ ID NO 58
<211> LENGTH: 50
<212> TYPE: DNA
<213> ORGANISM: Sus scrofa
<220> FEATURE:
<223> OTHER INFORMATION: ALGA0007591

<400> SEQUENCE: 58
ataaaaaatg agttggtgag tttgtacaag tcactcagct acccagtgtg         50

<210> SEQ ID NO 59
<211> LENGTH: 50
<212> TYPE: DNA
<213> ORGANISM: Sus scrofa
<220> FEATURE:
<223> OTHER INFORMATION: MARC0000195

<400> SEQUENCE: 59
ggaagccaat atgtaagata gtaaggtgac tcatctttca ttggtgcagc         50

<210> SEQ ID NO 60
<211> LENGTH: 50
<212> TYPE: DNA
<213> ORGANISM: Sus scrofa
<220> FEATURE:
<223> OTHER INFORMATION: ALGA0038697

<400> SEQUENCE: 60
caaagggtcc tttctcccca gtagagcccc taatgaagaa atgttcttgg         50

<210> SEQ ID NO 61
<211> LENGTH: 50
<212> TYPE: DNA
<213> ORGANISM: Sus scrofa
<220> FEATURE:
<223> OTHER INFORMATION: H3GA0020000

<400> SEQUENCE: 61
cagtaacaaa ttaccacaaa cttggtggct tgtaacaata gaaccgtgtt         50

<210> SEQ ID NO 62
<211> LENGTH: 50

```
<212> TYPE: DNA
<213> ORGANISM: Sus scrofa
<220> FEATURE:
<223> OTHER INFORMATION: ALGA0038703

<400> SEQUENCE: 62
acaaatatct catgctcatc ttgagccctc gtatgtgagg caaagtgtgg            50

<210> SEQ ID NO 63
<211> LENGTH: 50
<212> TYPE: DNA
<213> ORGANISM: Sus scrofa
<220> FEATURE:
<223> OTHER INFORMATION: H3GA0020002

<400> SEQUENCE: 63
aatattacaa ctagtttgac ttgctaagtg agagccaatc cacaaggccc            50

<210> SEQ ID NO 64
<211> LENGTH: 50
<212> TYPE: DNA
<213> ORGANISM: Sus scrofa
<220> FEATURE:
<223> OTHER INFORMATION: DRGA0007138

<400> SEQUENCE: 64
ttccttatat aaaacagtat agtatctgca tataacctat acacgtcctc            50

<210> SEQ ID NO 65
<211> LENGTH: 50
<212> TYPE: DNA
<213> ORGANISM: Sus scrofa
<220> FEATURE:
<223> OTHER INFORMATION: ASGA0031284

<400> SEQUENCE: 65
tccaagtctc agccgacttg ggaaatggaa atccccagat gatacctcag            50

<210> SEQ ID NO 66
<211> LENGTH: 50
<212> TYPE: DNA
<213> ORGANISM: Sus scrofa
<220> FEATURE:
<223> OTHER INFORMATION: ASGA0031285

<400> SEQUENCE: 66
ggtgagtcac tcaaatgaga acaaaggagc aggatgggtg gagctaggag            50

<210> SEQ ID NO 67
<211> LENGTH: 50
<212> TYPE: DNA
<213> ORGANISM: Sus scrofa
<220> FEATURE:
<223> OTHER INFORMATION: MARC0025042

<400> SEQUENCE: 67
acacatcaca gaagggagaa atggagatat aggatgagga cctgaacccc            50

<210> SEQ ID NO 68
<211> LENGTH: 50
<212> TYPE: DNA
<213> ORGANISM: Sus scrofa
<220> FEATURE:
<223> OTHER INFORMATION: H3GA0020006

<400> SEQUENCE: 68
```
aaagtaactg ccgaaggaca tgaactaatg aaagaaataa aaagggcccc       50

<210> SEQ ID NO 69
<211> LENGTH: 50
<212> TYPE: DNA
<213> ORGANISM: Sus scrofa
<220> FEATURE:
<223> OTHER INFORMATION: ALGA0038729

<400> SEQUENCE: 69
ttctggccac atgtacagtt ctgtgagtca tcctggctgt ggccagtgac       50

<210> SEQ ID NO 70
<211> LENGTH: 50
<212> TYPE: DNA
<213> ORGANISM: Sus scrofa
<220> FEATURE:
<223> OTHER INFORMATION: ALGA0038731

<400> SEQUENCE: 70
tgctttgaat cccaaccatg ccatgaccat tttgtagctc atttcaacct       50

<210> SEQ ID NO 71
<211> LENGTH: 50
<212> TYPE: DNA
<213> ORGANISM: Sus scrofa
<220> FEATURE:
<223> OTHER INFORMATION: ASGA0031321

<400> SEQUENCE: 71
ttgatgattg aagtttccag ctcgctgacc actctttctt cacctccctc       50

<210> SEQ ID NO 72
<211> LENGTH: 50
<212> TYPE: DNA
<213> ORGANISM: Sus scrofa
<220> FEATURE:
<223> OTHER INFORMATION: ASGA0031322

<400> SEQUENCE: 72
aagagaaaat agcaaacatg tccaaaagta gatcataagc tcccatgtcc       50

<210> SEQ ID NO 73
<211> LENGTH: 50
<212> TYPE: DNA
<213> ORGANISM: Sus scrofa
<220> FEATURE:
<223> OTHER INFORMATION: ALGA0038747

<400> SEQUENCE: 73
tgtggagaac agtttggcag ctcctcaaaa ggtcaaacct aaagtcacca       50

<210> SEQ ID NO 74
<211> LENGTH: 50
<212> TYPE: DNA
<213> ORGANISM: Sus scrofa
<220> FEATURE:
<223> OTHER INFORMATION: ASGA0033095

<400> SEQUENCE: 74
cgcataggaa ggaaagccga ggtgcgcagg ttaacagcca gtcagctctc       50

<210> SEQ ID NO 75
<211> LENGTH: 50
<212> TYPE: DNA
<213> ORGANISM: Sus scrofa

<220> FEATURE:
<223> OTHER INFORMATION: ALGA0040854

<400> SEQUENCE: 75
tagggaatta tccaacctaa ggtagtctat ggagatgcct gaatttgtag              50

<210> SEQ ID NO 76
<211> LENGTH: 50
<212> TYPE: DNA
<213> ORGANISM: Sus scrofa
<220> FEATURE:
<223> OTHER INFORMATION: ALGA0040856

<400> SEQUENCE: 76
ttaaacagtt aatcatctag gttttattta tagtaccatt ttccagcttg              50

<210> SEQ ID NO 77
<211> LENGTH: 50
<212> TYPE: DNA
<213> ORGANISM: Sus scrofa
<220> FEATURE:
<223> OTHER INFORMATION: ALGA0040857

<400> SEQUENCE: 77
atgccatagg caccgcaata gcagatccca gccgtacctg tgacttaaca              50

<210> SEQ ID NO 78
<211> LENGTH: 50
<212> TYPE: DNA
<213> ORGANISM: Sus scrofa
<220> FEATURE:
<223> OTHER INFORMATION: ASGA0033096

<400> SEQUENCE: 78
aggagtatca tgcctgaatt acacagctga taaatagcag ggattcagag              50

<210> SEQ ID NO 79
<211> LENGTH: 50
<212> TYPE: DNA
<213> ORGANISM: Sus scrofa
<220> FEATURE:
<223> OTHER INFORMATION: INRA0025180

<400> SEQUENCE: 79
agcaaggcag gatgtgatga ggaaggagcc aagaaaagta gactgcagac              50

<210> SEQ ID NO 80
<211> LENGTH: 50
<212> TYPE: DNA
<213> ORGANISM: Sus scrofa
<220> FEATURE:
<223> OTHER INFORMATION: ALGA0040859

<400> SEQUENCE: 80
gcttccctca cgctttacac ctgtccctag ctgctccact ggaggaggtg              50

<210> SEQ ID NO 81
<211> LENGTH: 50
<212> TYPE: DNA
<213> ORGANISM: Sus scrofa
<220> FEATURE:
<223> OTHER INFORMATION: H3GA0021216

<400> SEQUENCE: 81
aatatgttac aatacaagaa aaggggaat ccgcaacttg gacattggca              50

<210> SEQ ID NO 82
<211> LENGTH: 50
<212> TYPE: DNA
<213> ORGANISM: Sus scrofa
<220> FEATURE:
<223> OTHER INFORMATION: ASGA0033098

<400> SEQUENCE: 82
aggtaaaggt ttctatttgt ctctgagaag tcaagttccc tgttagctac        50

<210> SEQ ID NO 83
<211> LENGTH: 50
<212> TYPE: DNA
<213> ORGANISM: Sus scrofa
<220> FEATURE:
<223> OTHER INFORMATION: H3GA0021221

<400> SEQUENCE: 83
tatagaatat tccaatctgg aaaatctggg agttccttgt tggtctagtg        50

<210> SEQ ID NO 84
<211> LENGTH: 50
<212> TYPE: DNA
<213> ORGANISM: Sus scrofa
<220> FEATURE:
<223> OTHER INFORMATION: MARC0014540

<400> SEQUENCE: 84
accctctata ttcccttgaa gtcttatcta cggagacatc cttttgctgt        50

<210> SEQ ID NO 85
<211> LENGTH: 50
<212> TYPE: DNA
<213> ORGANISM: Sus scrofa
<220> FEATURE:
<223> OTHER INFORMATION: ASGA0033103

<400> SEQUENCE: 85
atggaagttg ccaggctagg ggtccaatca gagctgatgc cacccaacta        50

<210> SEQ ID NO 86
<211> LENGTH: 50
<212> TYPE: DNA
<213> ORGANISM: Sus scrofa
<220> FEATURE:
<223> OTHER INFORMATION: DIAS0000557

<400> SEQUENCE: 86
atgttctttc ctgggggtgc acagcctgtg ctgaggatgt ggtcgtagtt        50

<210> SEQ ID NO 87
<211> LENGTH: 50
<212> TYPE: DNA
<213> ORGANISM: Sus scrofa
<220> FEATURE:
<223> OTHER INFORMATION: ASGA0033116

<400> SEQUENCE: 87
catcagaact gctgcacaga tctccaatag ctccaggagg aagagtttaa        50

<210> SEQ ID NO 88
<211> LENGTH: 50
<212> TYPE: DNA
<213> ORGANISM: Sus scrofa
<220> FEATURE:
<223> OTHER INFORMATION: ASGA0036835

```
<400> SEQUENCE: 88
ctgccaagga gactgagagc tctcaggatt attgtatatt tgcccaagac                    50

<210> SEQ ID NO 89
<211> LENGTH: 50
<212> TYPE: DNA
<213> ORGANISM: Sus scrofa
<220> FEATURE:
<223> OTHER INFORMATION: MARC0031932

<400> SEQUENCE: 89
taaaattgct gattattttg atcactaata atggtaatgc aaagtcactc                    50

<210> SEQ ID NO 90
<211> LENGTH: 50
<212> TYPE: DNA
<213> ORGANISM: Sus scrofa
<220> FEATURE:
<223> OTHER INFORMATION: ASGA0036838

<400> SEQUENCE: 90
atcatgtagt taaattcgtc cacccagtgc aggtttcagt atctaccaaa                    50

<210> SEQ ID NO 91
<211> LENGTH: 50
<212> TYPE: DNA
<213> ORGANISM: Sus scrofa
<220> FEATURE:
<223> OTHER INFORMATION: H3GA0023523

<400> SEQUENCE: 91
attaacagaa tgaaagccaa tcaggggagg ccatgattct agagtggcta                    50

<210> SEQ ID NO 92
<211> LENGTH: 50
<212> TYPE: DNA
<213> ORGANISM: Sus scrofa
<220> FEATURE:
<223> OTHER INFORMATION: ALGA0045460

<400> SEQUENCE: 92
atcctatttg ccagtctcac acactcactg gaaggagcta tagaggaagt                    50

<210> SEQ ID NO 93
<211> LENGTH: 50
<212> TYPE: DNA
<213> ORGANISM: Sus scrofa
<220> FEATURE:
<223> OTHER INFORMATION: MARC0005927

<400> SEQUENCE: 93
caggtcctac tgatgcaaac cttcaactta taactaacca gtgacctaat                    50

<210> SEQ ID NO 94
<211> LENGTH: 50
<212> TYPE: DNA
<213> ORGANISM: Sus scrofa
<220> FEATURE:
<223> OTHER INFORMATION: MARC0005928

<400> SEQUENCE: 94
cagaaagatg ttaagtgcag gtgagagaag aggatttggg aagaaaaatt                    50

<210> SEQ ID NO 95
```

<211> LENGTH: 50
<212> TYPE: DNA
<213> ORGANISM: Sus scrofa
<220> FEATURE:
<223> OTHER INFORMATION: ASGA0036842

<400> SEQUENCE: 95
aatatggaca tgaggttggc aggagagcta ttctactgtg ggaactgtct          50

<210> SEQ ID NO 96
<211> LENGTH: 50
<212> TYPE: DNA
<213> ORGANISM: Sus scrofa
<220> FEATURE:
<223> OTHER INFORMATION: ASGA0036846

<400> SEQUENCE: 96
ggatgaacaa tattgtgtgt acgtactgga aagattaac cccagctact           50

<210> SEQ ID NO 97
<211> LENGTH: 50
<212> TYPE: DNA
<213> ORGANISM: Sus scrofa
<220> FEATURE:
<223> OTHER INFORMATION: MARC0098637

<400> SEQUENCE: 97
cacatgaaat gaactttaa ataaaatggt atttcctaca atgagttcca           50

<210> SEQ ID NO 98
<211> LENGTH: 50
<212> TYPE: DNA
<213> ORGANISM: Sus scrofa
<220> FEATURE:
<223> OTHER INFORMATION: M1GA0011035

<400> SEQUENCE: 98
gatttgatgc tatgcccggg cattgaaatt tctttagaaa ctaatgatat          50

<210> SEQ ID NO 99
<211> LENGTH: 50
<212> TYPE: DNA
<213> ORGANISM: Sus scrofa
<220> FEATURE:
<223> OTHER INFORMATION: DRGA0008230

<400> SEQUENCE: 99
aattaaagca aaggcattag taagagttta aaaggtttgt gctacaaagt          50

<210> SEQ ID NO 100
<211> LENGTH: 50
<212> TYPE: DNA
<213> ORGANISM: Sus scrofa
<220> FEATURE:
<223> OTHER INFORMATION: ASGA0036855

<400> SEQUENCE: 100
tagcagattt tgccttatct acccaattgc ctgtaagctg agggatggca          50

<210> SEQ ID NO 101
<211> LENGTH: 50
<212> TYPE: DNA
<213> ORGANISM: Sus scrofa
<220> FEATURE:
<223> OTHER INFORMATION: ALGA0097277

<400> SEQUENCE: 101
atcaatgggt tgaatatcta acaggcatgt ttctctgtgt cctccagtct          50

<210> SEQ ID NO 102
<211> LENGTH: 50
<212> TYPE: DNA
<213> ORGANISM: Sus scrofa
<220> FEATURE:
<223> OTHER INFORMATION: MARC0080197

<400> SEQUENCE: 102
acagctgaat gacagtgtac aataatacaa acacttaaac aatgaaaagt          50

<210> SEQ ID NO 103
<211> LENGTH: 50
<212> TYPE: DNA
<213> ORGANISM: Sus scrofa
<220> FEATURE:
<223> OTHER INFORMATION: H3GA0050489

<400> SEQUENCE: 103
gcagctgtag ctctgatttg accccctaacc caggaagttc catatcctgc          50

<210> SEQ ID NO 104
<211> LENGTH: 50
<212> TYPE: DNA
<213> ORGANISM: Sus scrofa
<220> FEATURE:
<223> OTHER INFORMATION: ALGA0097281

<400> SEQUENCE: 104
cttctcaggg cttttccctg tgttcttgac tttccactgc catctctcac          50

<210> SEQ ID NO 105
<211> LENGTH: 50
<212> TYPE: DNA
<213> ORGANISM: Sus scrofa
<220> FEATURE:
<223> OTHER INFORMATION: H3GA0050490

<400> SEQUENCE: 105
gcccaggtcc cattgtcacc cgaactcgga gctgggactc ttccagtcct          50

<210> SEQ ID NO 106
<211> LENGTH: 50
<212> TYPE: DNA
<213> ORGANISM: Sus scrofa
<220> FEATURE:
<223> OTHER INFORMATION: ALGA0097282

<400> SEQUENCE: 106
cccaactggc ctggctgaaa tgataagggt gacttcctac cttactctta          50

<210> SEQ ID NO 107
<211> LENGTH: 50
<212> TYPE: DNA
<213> ORGANISM: Sus scrofa
<220> FEATURE:
<223> OTHER INFORMATION: ASGA0079089

<400> SEQUENCE: 107
tctacctgca acctcttcct actctaaact ctaatagcac tttatgcaga          50

<210> SEQ ID NO 108
<211> LENGTH: 50
<212> TYPE: DNA

```
<213> ORGANISM: Sus scrofa
<220> FEATURE:
<223> OTHER INFORMATION: INRA0055354

<400> SEQUENCE: 108
ggaatgagct gctacctggg gacacagcta gcctgagtga ttttatcatc          50

<210> SEQ ID NO 109
<211> LENGTH: 50
<212> TYPE: DNA
<213> ORGANISM: Sus scrofa
<220> FEATURE:
<223> OTHER INFORMATION: ASGA0079091

<400> SEQUENCE: 109
cctgtgcact ctcttcccca ttagcgcaga aaagaccatc catcaccagc          50

<210> SEQ ID NO 110
<211> LENGTH: 50
<212> TYPE: DNA
<213> ORGANISM: Sus scrofa
<220> FEATURE:
<223> OTHER INFORMATION: ASGA0079090

<400> SEQUENCE: 110
ttcacccact gtattgagaa agtaccaata ccaacacaaa gagcttcgtg          50

<210> SEQ ID NO 111
<211> LENGTH: 50
<212> TYPE: DNA
<213> ORGANISM: Sus scrofa
<220> FEATURE:
<223> OTHER INFORMATION: H3GA0050491

<400> SEQUENCE: 111
ttcaagccgc agttgtgacc tacgctgcag ctgtggcaat gccggatcct          50

<210> SEQ ID NO 112
<211> LENGTH: 50
<212> TYPE: DNA
<213> ORGANISM: Sus scrofa
<220> FEATURE:
<223> OTHER INFORMATION: MARC0056017

<400> SEQUENCE: 112
actaattcct tagccagaga cataaacagg cacagagctg tagttgccct          50

<210> SEQ ID NO 113
<211> LENGTH: 50
<212> TYPE: DNA
<213> ORGANISM: Sus scrofa
<220> FEATURE:
<223> OTHER INFORMATION: MARC0055759

<400> SEQUENCE: 113
ggagctttct ctgcaagctt cctggtcacc catcactgct tgaggacaca          50

<210> SEQ ID NO 114
<211> LENGTH: 50
<212> TYPE: DNA
<213> ORGANISM: Sus scrofa
<220> FEATURE:
<223> OTHER INFORMATION: H3GA0050495

<400> SEQUENCE: 114
gaagaatatg taagcataaa tttaaaggcc cctagaggaa gacaatatat          50
```

<210> SEQ ID NO 115
<211> LENGTH: 50
<212> TYPE: DNA
<213> ORGANISM: Sus scrofa
<220> FEATURE:
<223> OTHER INFORMATION: ALGA0097291

<400> SEQUENCE: 115
caactccaaa tataacaact ttaatggtcc tcacttagct ttaggattcc         50

<210> SEQ ID NO 116
<211> LENGTH: 50
<212> TYPE: DNA
<213> ORGANISM: Sus scrofa
<220> FEATURE:
<223> OTHER INFORMATION: ALGA0097290

<400> SEQUENCE: 116
cggaggcata gctttgatcc ccagctccgt gcagtgtgtt acaggatctg         50

<210> SEQ ID NO 117
<211> LENGTH: 50
<212> TYPE: DNA
<213> ORGANISM: Sus scrofa
<220> FEATURE:
<223> OTHER INFORMATION: CASI0006683

<400> SEQUENCE: 117
gacagtttct aaccaaacta gagtagcaaa atttgagttc aagttgtagt         50

<210> SEQ ID NO 118
<211> LENGTH: 50
<212> TYPE: DNA
<213> ORGANISM: Sus scrofa
<220> FEATURE:
<223> OTHER INFORMATION: ASGA0079098

<400> SEQUENCE: 118
catgagtggg caagaacaca cagcttgttc ctgaggtgat gactggaagc         50

<210> SEQ ID NO 119
<211> LENGTH: 50
<212> TYPE: DNA
<213> ORGANISM: Sus scrofa
<220> FEATURE:
<223> OTHER INFORMATION: ALGA0097297

<400> SEQUENCE: 119
gcctttgagt ttaggagcca gctatatgga aaaatctaaa tgtctcagca         50

<210> SEQ ID NO 120
<211> LENGTH: 50
<212> TYPE: DNA
<213> ORGANISM: Sus scrofa
<220> FEATURE:
<223> OTHER INFORMATION: H3GA0054426

<400> SEQUENCE: 120
ggagggaggg atcaggacct aagtagggcc attctggaca agtgggcaaa         50

<210> SEQ ID NO 121
<211> LENGTH: 50
<212> TYPE: DNA
<213> ORGANISM: Sus scrofa
<220> FEATURE:

<223> OTHER INFORMATION: ALGA0098112

<400> SEQUENCE: 121
tcaaacatcc ttattttctt ttctattttt ctctcctata ctctagccgg    50

<210> SEQ ID NO 122
<211> LENGTH: 50
<212> TYPE: DNA
<213> ORGANISM: Sus scrofa
<220> FEATURE:
<223> OTHER INFORMATION: MARC0089391

<400> SEQUENCE: 122
tctggcagcc ggctatagag ggataggagg gcaaggagct caatggtctg    50

<210> SEQ ID NO 123
<211> LENGTH: 50
<212> TYPE: DNA
<213> ORGANISM: Sus scrofa
<220> FEATURE:
<223> OTHER INFORMATION: ASGA0089892

<400> SEQUENCE: 123
tggaggtgat agtccagcca agcattgaag gacggaaggg ggttaggaca    50

<210> SEQ ID NO 124
<211> LENGTH: 50
<212> TYPE: DNA
<213> ORGANISM: Sus scrofa
<220> FEATURE:
<223> OTHER INFORMATION: ASGA0097792

<400> SEQUENCE: 124
ggggcctcta agccacctgt cactcatcct ctttcctggc ccagaggttt    50

<210> SEQ ID NO 125
<211> LENGTH: 50
<212> TYPE: DNA
<213> ORGANISM: Sus scrofa
<220> FEATURE:
<223> OTHER INFORMATION: MARC0046857

<400> SEQUENCE: 125
gagtaaaggg ctttgaagga gaagattact gttctctctt tgaaatgttt    50

<210> SEQ ID NO 126
<211> LENGTH: 50
<212> TYPE: DNA
<213> ORGANISM: Sus scrofa
<220> FEATURE:
<223> OTHER INFORMATION: MARC0077194

<400> SEQUENCE: 126
aactcaggaa agtgtaaccc aggtgtcctc aaagagaagg ggggagattg    50

<210> SEQ ID NO 127
<211> LENGTH: 50
<212> TYPE: DNA
<213> ORGANISM: Sus scrofa
<220> FEATURE:
<223> OTHER INFORMATION: ALGA0108769

<400> SEQUENCE: 127
gaggcatgct gtagtatctt tcagccatta cctgggagca ggttactgag    50

```
<210> SEQ ID NO 128
<211> LENGTH: 50
<212> TYPE: DNA
<213> ORGANISM: Sus scrofa
<220> FEATURE:
<223> OTHER INFORMATION: H3GA0050799

<400> SEQUENCE: 128
gcaggatata aacagatata tagatgtaat caagcttcct cctccaccaa        50

<210> SEQ ID NO 129
<211> LENGTH: 50
<212> TYPE: DNA
<213> ORGANISM: Sus scrofa
<220> FEATURE:
<223> OTHER INFORMATION: ALGA0098120

<400> SEQUENCE: 129
cctggaagtg ggccagactg tagataaagc gtttgatgtg tcagcagtag        50

<210> SEQ ID NO 130
<211> LENGTH: 50
<212> TYPE: DNA
<213> ORGANISM: Sus scrofa
<220> FEATURE:
<223> OTHER INFORMATION: ALGA0098123

<400> SEQUENCE: 130
cccaacacag tgtcatgagg atgtgggttc aatccctgcc ctcactcagt        50

<210> SEQ ID NO 131
<211> LENGTH: 50
<212> TYPE: DNA
<213> ORGANISM: Sus scrofa
<220> FEATURE:
<223> OTHER INFORMATION: ALGA0098128

<400> SEQUENCE: 131
ctttgtttta ggagggagtc ctcagccaag tctagctaga tggggatagt        50

<210> SEQ ID NO 132
<211> LENGTH: 50
<212> TYPE: DNA
<213> ORGANISM: Sus scrofa
<220> FEATURE:
<223> OTHER INFORMATION: ASGA0079719

<400> SEQUENCE: 132
cctctagaaa ccttgaaggc tcttgcattc tttcttggag cccagcttcc        50

<210> SEQ ID NO 133
<211> LENGTH: 50
<212> TYPE: DNA
<213> ORGANISM: Sus scrofa
<220> FEATURE:
<223> OTHER INFORMATION: ASGA0079728

<400> SEQUENCE: 133
gtcttatcaa atgtgacctg cttctggcca tgcagggtgg gaagaatgtg        50

<210> SEQ ID NO 134
<211> LENGTH: 50
<212> TYPE: DNA
<213> ORGANISM: Sus scrofa
<220> FEATURE:
<223> OTHER INFORMATION: ASGA0080429
```

```
<400> SEQUENCE: 134
gatttaggaa agcactgagt atcagccatc cagccaaggt aggtacagga            50

<210> SEQ ID NO 135
<211> LENGTH: 50
<212> TYPE: DNA
<213> ORGANISM: Sus scrofa
<220> FEATURE:
<223> OTHER INFORMATION: MARC0052755

<400> SEQUENCE: 135
ttctcataca ccatccaata aacactgacc acatcctgac cagagctaag            50

<210> SEQ ID NO 136
<211> LENGTH: 50
<212> TYPE: DNA
<213> ORGANISM: Sus scrofa
<220> FEATURE:
<223> OTHER INFORMATION: ALGA0098918

<400> SEQUENCE: 136
tctgcatgta atttagtgca gagtgccaga atcccgagta gctgggttcc            50

<210> SEQ ID NO 137
<211> LENGTH: 50
<212> TYPE: DNA
<213> ORGANISM: Sus scrofa
<220> FEATURE:
<223> OTHER INFORMATION: ASGA0080432

<400> SEQUENCE: 137
ggaagccatt ttcctcctcc cgtggacaca atgaatgtgc agctacacac            50

<210> SEQ ID NO 138
<211> LENGTH: 50
<212> TYPE: DNA
<213> ORGANISM: Sus scrofa
<220> FEATURE:
<223> OTHER INFORMATION: ALGA0098922

<400> SEQUENCE: 138
aaattttaag ttaaaacaag ctgtgcccag aggaacatat agtctggctc            50

<210> SEQ ID NO 139
<211> LENGTH: 50
<212> TYPE: DNA
<213> ORGANISM: Sus scrofa
<220> FEATURE:
<223> OTHER INFORMATION: INRA0056206

<400> SEQUENCE: 139
aaccgaaatt gtgttttcat ccctgagttt ccaactgttc tatttaagca            50

<210> SEQ ID NO 140
<211> LENGTH: 50
<212> TYPE: DNA
<213> ORGANISM: Sus scrofa
<220> FEATURE:
<223> OTHER INFORMATION: INRA0056207

<400> SEQUENCE: 140
taatcctgaa aatagccggg aaaattcttg aaagagaagg acagtttggg            50

<210> SEQ ID NO 141
<211> LENGTH: 50
```

<210> SEQ ID NO 141
<211> LENGTH: 50
<212> TYPE: DNA
<213> ORGANISM: Sus scrofa
<220> FEATURE:
<223> OTHER INFORMATION: ASGA0080435

<400> SEQUENCE: 141
gatatattta catgtgggac tgagtcactc ggctgcacac ctgaagctaa    50

<210> SEQ ID NO 142
<211> LENGTH: 50
<212> TYPE: DNA
<213> ORGANISM: Sus scrofa
<220> FEATURE:
<223> OTHER INFORMATION: MARC0068495

<400> SEQUENCE: 142
aaatctagag gtgggaaact ttgagacagc ctattccatt agacttggga    50

<210> SEQ ID NO 143
<211> LENGTH: 50
<212> TYPE: DNA
<213> ORGANISM: Sus scrofa
<220> FEATURE:
<223> OTHER INFORMATION: ASGA0080436

<400> SEQUENCE: 143
ttaatcaact tcagacattt cctctttgcc tcctgctttg acgaaaaggc    50

<210> SEQ ID NO 144
<211> LENGTH: 50
<212> TYPE: DNA
<213> ORGANISM: Sus scrofa
<220> FEATURE:
<223> OTHER INFORMATION: MARC0003370

<400> SEQUENCE: 144
ccttccattg gctctagaat aagctccgga ttgtacaaat ctgactcggt    50

<210> SEQ ID NO 145
<211> LENGTH: 50
<212> TYPE: DNA
<213> ORGANISM: Sus scrofa
<220> FEATURE:
<223> OTHER INFORMATION: ASGA0085659

<400> SEQUENCE: 145
agttggtttc gttgctgctg agccacaaca ggaattcata ttaagaacat    50

METHOD FOR IDENTIFYING WUZHISHAN MINIATURE PIG INBRED LINE BY USING 145 SNPS

CROSS-REFERENCE TO RELATED APPLICATIONS

The present application is a U.S. National Phase of International Patent Application Serial No. PCT/CN2014/000937 entitled "METHOD FOR IDENTIFYING WUZHISHAN MINIATURE PIG INBRED LINE BY USING 145 SNP," filed on Oct. 21, 2014. The entire contents of the above-referenced application are hereby incorporated by reference for all purposes.

INCORPORATION BY REFERENCE OF ELECTRONICALLY SUBMITTED MATERIAL

Incorporated by reference in its entirety herein is a computer-readable nucleotide sequence listing submitted herewith and identified as follows: 24,964 bytes ASCII (Text) file named "Sequence_Listing_JEE17305PCTUS," created Apr. 21, 2017.

TECHNICAL FIELD

The present invention relates to a method for identifying Wuzhishan miniature pig inbred line by using 145 SNPs.

BACKGROUND

During the period of 1989-2003, under the support from seven related programs including the $7^{th}$, $8^{th}$ and $9^{th}$ Five-Year key industrial R & D Programs of China's Ministry of Agriculture, and "Chinese National Programs for High Technology Research and Development Program (863 Program)" of China's Ministry of Science and Technology, key and major projects of National Natural Science Foundation of China etc., the research working on "the breeding, germplasm characteristics, as well as development and utilization of Wuzhishan inbred line" had made many breakthroughs, including but not limited to, taking a boar and a sow from Wuzhishan pigs (also referred as Wuzhishan miniature pigs) as line ancestors, continuously employing "offspring-parent", "full sibs" mating, and other comprehensive measures, gradually overcoming the adverse effects that inbreeding resulted in very low breeding survival rate, which was less than 20% at that time, establishing $F_{17}$ inbred line population and genealogy, monitoring the research process of inbred line breeding of inbred line varieties $F_7$-$F_{16}$ by using many advanced technical means, such as molecularly genetic means, DNA fingerprinting similarity factor, microsatellite etc., preliminarily revealing genetic regularity and characteristics of Wuzhishan miniature pig inbred line, and demonstrating the facticity and scientificity of the breeding process of this inbred line. Moreover, many studies on exploitation and utilization of Wuzhishan miniature pig inbred line had been completed, showing the incomparable superiority of this inbred line in serving as an ideal animal model for human disease, and consequently achieving a certain economic benefits and major social benefits. Two achievements of the researches—"Researches on germplasm characteristics as well as exploitation and utilization of Wuzhishan miniature pigs" (Achievements Appraisal of Academy of Agricultural Sciences 【95】, No. 075) and "Wuzhishan miniature pig inbred line breeding for experiments and molecule genetic basic research" passed the Science and Technology Achievement Appraisals hosted by China's Ministry of Agriculture in 1995 and 2005 respectively, and won the Third Prize of China's Ministry of Agriculture Science and Technology Progress Award in 1999.

Preliminary research achievements of miniature pig inbred breeding had great influences at home and abroad. For example, industrial specialists from the United States, Italy, Japan, West Germany, Korea, and other countries had proposed for introduction and cultivation, and or cooperative study. An institute of the United States proposed to purchase 50 boars with 5 million USD in 1996; Korea proposed to cooperatively set up factories in China by funding 5 million RMB in 2000 after its introduction and cultivation proposal was rejected. The main reason behind the influences is that the inbred line animals, as special genetic resources for animals, can rapidly obtain scientific data for life science researches with the same extent of sensitivity and accuracy as from analytical reagents in chemistry and precise instruments in physics. With their very high use value and research significance, more than 450 inbred lines of mice, rats, and small mammals etc, have been bred in the world at present, and widely used as animal models for studying difficult and complicated human diseases, solving difficult problems in bioscience, medical science, and pharmaceutics, and other research fields. Due to the various differences between pigs and those small animals in interspecific physiology, the breeding of inbred line pigs has been very difficult. It was verified by novelty searching (2013. 11) that there was no successful report in the world. Moreover, compared with rodents, pigs possesses greater similarity with human, and will play irreplaceable, unique roles in the researches for studying difficult and complicated human diseases and solving difficult problems in bioscience, medical science, and pharmaceutics. Inbred line pigs are rare, valuable genetic resources of large animals in the world. Previously, in 1960s, many departments of the United States and Europe carried out the breeding research of inbred line pigs, but failed with the highest inbreeding coefficient no more than 0.75. After a 15-year breeding research, China has obtained $F_{17}$ with the special Chinese miniature pig resource, and the inbreeding coefficient is up to 0.965, and more encouragingly the high incidence stage of piglet death due to inbred breeding has been overcome. Therefore, the successful breeding of inbred line pigs will be likely achieved in China firstly. After a further work in current years, Wuzhishan miniature pig inbred lines $F_{17}$ to $F_{22}$ have been obtained.

Because there was no successful breeding report for inbred line pigs in the world yet, and either the standard of establishment or identification method of inbred line pigs does not exist, either, we strictly referred to and followed the breeding method of inbred line mouse or rat, that was, inbreeding more than 20 generations from two pigs in same ancestor and establishing complete genealogy, testing the genetic stability thereof, establishing identification method, establishing line standard, specially on interspecific differences from current Hainan Wuzhishan pigs. Only in this way, scientific and credible evidence can be provided to the industry and the world, and such novel innovation project of genetic resource can be accomplished, thereby to benefit human beings.

Once the miniature pig inbred line is successfully bred, China will possess the proprietary intellectual property rights and the international leading level of innovative genetic germplasm resource of pig, which will fill up research blank within this research field in the world, and enrich theory and practice of inbred line breeding for large animals. Meanwhile, as an ideal "animal models" for human beings, inbred line pig is an important foundation and innovation basis for the progress of biotechnological research, which will significantly promote collaborative development and innovation in bioscience, human medical science, and pharmacy, etc. in China, and play irreplaceable position for studying difficult and complicated human diseases, extending lives, so as to benefit human beings. Therefore, it possesses important practical and theoretical significance.

THE CONTENT OF THE INVENTION

The purpose of the present invention is to provide a method for identifying Wuzhishan miniature pig inbred line by using 145 SNPs.

The present invention provides a method for auxiliarily identifying whether the pig to be tested is inbred line of Wuzhishan miniature pig, comprising the following steps:

Testing genotypes based on 145 SNP sites of the pig to be tested;

If all the standards of the following (1) to (145) are satisfied, the pig to be tested is a candidate for Wuzhishan miniature pig inbred line:

(1) M1GA0025062 the genotype of SNP site is GG;
(2) DRGA0017627 the genotype of SNP site is GG;
(3) H3GA0056137 the genotype of SNP site is CC;
(4) MARC0039661 the genotype of SNP site is AA;
(5) ASGA0085025 the genotype of SNP site is TT;
(6) ASGA0098570 the genotype of SNP site is GG;
(7) MARC0063358 the genotype of SNP site is AA;
(8) ASGA0085437 the genotype of SNP site is GG;
(9) MARC0096709 the genotype of SNP site is CC;
(10) H3GA0052387 the genotype of SNP site is GG;
(11) ASGA0000264 the genotype of SNP site is TT;
(12) ALGA0000195 the genotype of SNP site is TT;
(13) H3GA0001444 the genotype of SNP site is AA;
(14) ASGA0002293 the genotype of SNP site is CC;
(15) INRA0001752 the genotype of SNP site is GG;
(16) H3GA0001445 the genotype of SNP site is GG;
(17) ALGA0002595 the genotype of SNP site is TT;
(18) ALGA0002600 the genotype of SNP site is GG;
(19) DRGA0000563 the genotype of SNP site is CC;
(20) DRGA0000565 the genotype of SNP site is CC;
(21) INRA0001761 the genotype of SNP site is AA;
(22) MARC0104045 the genotype of SNP site is CC;
(23) ALGA0002601 the genotype of SNP site is CC;
(24) DRGA0000569 the genotype of SNP site is AA;
(25) ALGA0002608 the genotype of SNP site is TT;
(26) DRGA0000568 the genotype of SNP site is CC;
(27) ALGA0002604 the genotype of SNP site is GG;
(28) MARC0048118 the genotype of SNP site is TT;
(29) ASGA0004229 the genotype of SNP site is CC;
(30) MARC0007088 the genotype of SNP site is CC;
(31) MARC0000061 the genotype of SNP site is GG;
(32) MARC0094747 the genotype of SNP site is AA;
(33) MARC0007969 the genotype of SNP site is AA;
(34) ASGA0106092 the genotype of SNP site is CC;
(35) ALGA0119806 the genotype of SNP site is GG;
(36) INRA0003745 the genotype of SNP site is AA;
(37) INRA0003746 the genotype of SNP site is TT;
(38) ALGA0005490 the genotype of SNP site is CC;
(39) H3GA0002538 the genotype of SNP site is CC;
(40) INRA0003749 the genotype of SNP site is CC;
(41) H3GA0002539 the genotype of SNP site is GG;
(42) M1GA0001099 the genotype of SNP site is CC;
(43) MARC0111831 the genotype of SNP site is AA;
(44) ASGA0005566 the genotype of SNP site is CC;
(45) ALGA0007578 the genotype of SNP site is CC;
(46) ASGA0005568 the genotype of SNP site is CC;
(47) INRA0005765 the genotype of SNP site is AA;
(48) MARC0095347 the genotype of SNP site is CC;
(49) MARC0039015 the genotype of SNP site is CC;
(50) DRGA0001892 the genotype of SNP site is GG;
(51) ALGA0007580 the genotype of SNP site is GG;
(52) ALGA0007583 the genotype of SNP site is TT;
(53) MARC0095915 the genotype of SNP site is CC;
(54) ASGA0005571 the genotype of SNP site is AA;
(55) MARC0014134 the genotype of SNP site is AA;
(56) MARC0024233 the genotype of SNP site is AA;
(57) H3GA0003548 the genotype of SNP site is GG;
(58) ALGA0007591 the genotype of SNP site is CC;
(59) MARC0000195 the genotype of SNP site is CC;
(60) ALGA0038697 the genotype of SNP site is CC;
(61) H3GA0020000 the genotype of SNP site is CC;
(62) ALGA0038703 the genotype of SNP site is CC;
(63) H3GA0020002 the genotype of SNP site is GG;
(64) DRGA0007138 the genotype of SNP site is CC;
(65) ASGA0031284 the genotype of SNP site is CC;
(66) ASGA0031285 the genotype of SNP site is AA;
(67) MARC0025042 the genotype of SNP site is GG;
(68) H3GA0020006 the genotype of SNP site is TT;
(69) ALGA0038729 the genotype of SNP site is CC;
(70) ALGA0038731 the genotype of SNP site is GG;
(71) ASGA0031321 the genotype of SNP site is GG;
(72) ASGA0031322 the genotype of SNP site is GG;
(73) ALGA0038747 the genotype of SNP site is AA;
(74) ASGA0033095 the genotype of SNP site is TT;
(75) ALGA0040854 the genotype of SNP site is GG;
(76) ALGA0040856 the genotype of SNP site is AA;
(77) ALGA0040857 the genotype of SNP site is GG;
(78) ASGA0033096 the genotype of SNP site is GG;
(79) INRA0025180 the genotype of SNP site is AA;
(80) ALGA0040859 the genotype of SNP site is CC;
(81) H3GA0021216 the genotype of SNP site is CC;
(82) ASGA0033098 the genotype of SNP site is CC;
(83) H3GA0021221 the genotype of SNP site is CC;
(84) MARC0014540 the genotype of SNP site is CC;
(85) ASGA0033103 the genotype of SNP site is CC;
(86) DIAS0000557 the genotype of SNP site is AA;
(87) ASGA0033116 the genotype of SNP site is AA;
(88) ASGA0036835 the genotype of SNP site is CC;
(89) MARC0031932 the genotype of SNP site is CC;
(90) ASGA0036838 the genotype of SNP site is CC;
(91) H3GA0023523 the genotype of SNP site is GG;
(92) ALGA0045460 the genotype of SNP site is TT;
(93) MARC0005927 the genotype of SNP site is GG;
(94) MARC0005928 the genotype of SNP site is AA;
(95) ASGA0036842 the genotype of SNP site is CC;
(96) ASGA0036846 the genotype of SNP site is CC;
(97) MARC0098637 the genotype of SNP site is TT;
(98) M1GA0011035 the genotype of SNP site is TT;
(99) DRGA0008230 the genotype of SNP site is GG;
(100) ASGA0036855 the genotype of SNP site is CC;
(101) ALGA0097277 the genotype of SNP site is GG;
(102) MARC0080197 the genotype of SNP site is CC;
(103) H3GA0050489 the genotype of SNP site is TT;
(104) ALGA0097281 the genotype of SNP site is TT;
(105) H3GA0050490 the genotype of SNP site is CC;
(106) ALGA0097282 the genotype of SNP site is TT;
(107) ASGA0079089 the genotype of SNP site is CC;
(108) INRA0055354 the genotype of SNP site is GG;
(109) ASGA0079091 the genotype of SNP site is TT;

(110) ASGA0079090 the genotype of SNP site is CC;
(111) H3GA0050491 the genotype of SNP site is AA;
(112) MARC0056017 the genotype of SNP site is TT;
(113) MARC0055759 the genotype of SNP site is AA;
(114) H3GA0050495 the genotype of SNP site is GG;
(115) ALGA0097291 the genotype of SNP site is GG;
(116) ALGA0097290 the genotype of SNP site is GG;
(117) CASI0006683 the genotype of SNP site is GG;
(118) ASGA0079098 the genotype of SNP site is CC;
(119) ALGA0097297 the genotype of SNP site is GG;
(120) H3GA0054426 the genotype of SNP site is TT;
(121) ALGA0098112 the genotype of SNP site is GG;
(122) MARC0089391 the genotype of SNP site is GG;
(123) ASGA0089892 the genotype of SNP site is AA;
(124) ASGA0097792 the genotype of SNP site is CC;
(125) MARC0046857 the genotype of SNP site is GG;
(126) MARC0077194 the genotype of SNP site is AA;
(127) ALGA0108769 the genotype of SNP site is CC;
(128) H3GA0050799 the genotype of SNP site is CC;
(129) ALGA0098120 the genotype of SNP site is CC;
(130) ALGA0098123 the genotype of SNP site is GG;
(131) ALGA0098128 the genotype of SNP site is GG;
(132) ASGA0079719 the genotype of SNP site is CC;
(133) ASGA0079728 the genotype of SNP site is GG;
(134) ASGA0080429 the genotype of SNP site is CC;
(135) MARC0052755 the genotype of SNP site is GG;
(136) ALGA0098918 the genotype of SNP site is GG;
(137) ASGA0080432 the genotype of SNP site is GG;
(138) ALGA0098922 the genotype of SNP site is CC;
(139) INRA0056206 the genotype of SNP site is GG;
(140) INRA0056207 the genotype of SNP site is CC;
(141) ASGA0080435 the genotype of SNP site is CC;
(142) MARC0068495 the genotype of SNP site is GG;
(143) ASGA0080436 the genotype of SNP site is CC;
(144) MARC0003370 the genotype of SNP site is CC;
(145) ASGA0085659 the genotype of SNP site is CC;

If any standard of the above is not satisfied, the pig to be tested is a candidate for non-Wuzhishan miniature pig inbred line.

The pig to be tested can be the Wuzhishan miniature pig inbred line or Hainan Wuzhishan pig.

The Wuzhishan miniature pig inbred line can belong to any one of $F_{20}$ to $F_{22}$ generations.

The Wuzhishan miniature pig inbred line can belong to $F_{20}$ generation or generations later than $F_{20}$ generation.

In this method, specific chips can be employed to test the genotype based on 145 SNP sites of the pig to be tested; the specific chips are nucleic acid chips in which single-stranded DNA molecules shown as Sequences 1-145 in the sequence listing are immobilized at different points, respectively.

The present invention is also used to protect a nucleic acid chip in which single-stranded DNA molecules shown as Sequences 1-145 in the sequence listing are immobilized at different points, respectively.

The present invention is also used to protect the use of the nucleic acid chip, which is the following (a) or (b): (a) auxiliarily identifying whether the pig to be tested is Wuzhishan miniature pig inbred line; or (b) auxiliarily identifying whether the pig population to be tested is Wuzhishan miniature pig inbred line population.

The pig to be tested can be the Wuzhishan miniature pig inbred line or Hainan Wuzhishan pig.

The Wuzhishan miniature pig inbred line can belong to any one of $F_{20}$ to $F_{22}$ generations.

The Wuzhishan miniature pig inbred line can belong to $F_{20}$ generation or generations later than $F_{20}$ generation.

The present invention also provides a method for auxiliarily identifying whether the pig population to be tested is Wuzhishan miniature pig inbred line population, comprising the following steps:

Randomly sampling from the pig population to be tested to obtain samples to be tested, then testing the genotypes based on 145 SNP sites of each of samples to be tested, and if all the samples to be tested satisfy all the standards of the following (1) to (145), the pig population to be tested is a candidate for Wuzhishan miniature pig inbred line population:

(1) M1GA0025062 the genotype of SNP site is GG;
(2) DRGA0017627 the genotype of SNP site is GG;
(3) H3GA0056137 the genotype of SNP site is CC;
(4) MARC0039661 the genotype of SNP site is AA;
(5) ASGA0085025 the genotype of SNP site is TT;
(6) ASGA0098570 the genotype of SNP site is GG;
(7) MARC0063358 the genotype of SNP site is AA;
(8) ASGA0085437 the genotype of SNP site is GG;
(9) MARC0096709 the genotype of SNP site is CC;
(10) H3GA0052387 the genotype of SNP site is GG;
(11) ASGA0000264 the genotype of SNP site is TT;
(12) ALGA0000195 the genotype of SNP site is TT;
(13) H3GA0001444 the genotype of SNP site is AA;
(14) ASGA0002293 the genotype of SNP site is CC;
(15) INRA0001752 the genotype of SNP site is GG;
(16) H3GA0001445 the genotype of SNP site is GG;
(17) ALGA0002595 the genotype of SNP site is TT;
(18) ALGA0002600 the genotype of SNP site is GG;
(19) DRGA0000563 the genotype of SNP site is CC;
(20) DRGA0000565 the genotype of SNP site is CC;
(21) INRA0001761 the genotype of SNP site is AA;
(22) MARC0104045 the genotype of SNP site is CC;
(23) ALGA0002601 the genotype of SNP site is CC;
(24) DRGA0000569 the genotype of SNP site is AA;
(25) ALGA0002608 the genotype of SNP site is TT;
(26) DRGA0000568 the genotype of SNP site is CC;
(27) ALGA0002604 the genotype of SNP site is GG;
(28) MARC0048118 the genotype of SNP site is TT;
(29) ASGA0004229 the genotype of SNP site is CC;
(30) MARC0007088 the genotype of SNP site is CC;
(31) MARC0000061 the genotype of SNP site is GG;
(32) MARC0094747 the genotype of SNP site is AA;
(33) MARC0007969 the genotype of SNP site is AA;
(34) ASGA0106092 the genotype of SNP site is CC;
(35) ALGA0119806 the genotype of SNP site is GG;
(36) INRA0003745 the genotype of SNP site is AA;
(37) INRA0003746 the genotype of SNP site is TT;
(38) ALGA0005490 the genotype of SNP site is CC;
(39) H3GA0002538 the genotype of SNP site is CC;
(40) INRA0003749 the genotype of SNP site is CC;
(41) H3GA0002539 the genotype of SNP site is GG;
(42) M1GA0001099 the genotype of SNP site is CC;
(43) MARC0111831 the genotype of SNP site is AA;
(44) ASGA0005566 the genotype of SNP site is CC;
(45) ALGA0007578 the genotype of SNP site is CC;
(46) ASGA0005568 the genotype of SNP site is CC;
(47) INRA0005765 the genotype of SNP site is AA;
(48) MARC0095347 the genotype of SNP site is CC;
(49) MARC0039015 the genotype of SNP site is CC;
(50) DRGA0001892 the genotype of SNP site is GG;
(51) ALGA0007580 the genotype of SNP site is GG;
(52) ALGA0007583 the genotype of SNP site is TT;
(53) MARC0095915 the genotype of SNP site is CC;
(54) ASGA0005571 the genotype of SNP site is AA;
(55) MARC0014134 the genotype of SNP site is AA;
(56) MARC0024233 the genotype of SNP site is AA;

(57) H3GA0003548 the genotype of SNP site is GG;
(58) ALGA0007591 the genotype of SNP site is CC;
(59) MARC0000195 the genotype of SNP site is CC;
(60) ALGA0038697 the genotype of SNP site is CC;
(61) H3GA0020000 the genotype of SNP site is CC;
(62) ALGA0038703 the genotype of SNP site is CC;
(63) H3GA0020002 the genotype of SNP site is GG;
(64) DRGA0007138 the genotype of SNP site is CC;
(65) ASGA0031284 the genotype of SNP site is CC;
(66) ASGA0031285 the genotype of SNP site is AA;
(67) MARC0025042 the genotype of SNP site is GG;
(68) H3GA0020006 the genotype of SNP site is TT;
(69) ALGA0038729 the genotype of SNP site is CC;
(70) ALGA0038731 the genotype of SNP site is GG;
(71) ASGA0031321 the genotype of SNP site is GG;
(72) ASGA0031322 the genotype of SNP site is GG;
(73) ALGA0038747 the genotype of SNP site is AA;
(74) ASGA0033095 the genotype of SNP site is TT;
(75) ALGA0040854 the genotype of SNP site is GG;
(76) ALGA0040856 the genotype of SNP site is AA;
(77) ALGA0040857 the genotype of SNP site is GG;
(78) ASGA0033096 the genotype of SNP site is GG;
(79) INRA0025180 the genotype of SNP site is AA;
(80) ALGA0040859 the genotype of SNP site is CC;
(81) H3GA0021216 the genotype of SNP site is CC;
(82) ASGA0033098 the genotype of SNP site is CC;
(83) H3GA0021221 the genotype of SNP site is CC;
(84) MARC0014540 the genotype of SNP site is CC;
(85) ASGA0033103 the genotype of SNP site is CC;
(86) DIAS0000557 the genotype of SNP site is AA;
(87) ASGA0033116 the genotype of SNP site is AA;
(88) ASGA0036835 the genotype of SNP site is CC;
(89) MARC0031932 the genotype of SNP site is CC;
(90) ASGA0036838 the genotype of SNP site is CC;
(91) H3GA0023523 the genotype of SNP site is GG;
(92) ALGA0045460 the genotype of SNP site is TT;
(93) MARC0005927 the genotype of SNP site is GG;
(94) MARC0005928 the genotype of SNP site is AA;
(95) ASGA0036842 the genotype of SNP site is CC;
(96) ASGA0036846 the genotype of SNP site is CC;
(97) MARC0098637 the genotype of SNP site is TT;
(98) M1GA0011035 the genotype of SNP site is TT;
(99) DRGA0008230 the genotype of SNP site is GG;
(100) ASGA0036855 the genotype of SNP site is CC;
(101) ALGA0097277 the genotype of SNP site is GG;
(102) MARC0080197 the genotype of SNP site is CC;
(103) H3GA0050489 the genotype of SNP site is TT;
(104) ALGA0097281 the genotype of SNP site is TT;
(105) H3GA0050490 the genotype of SNP site is CC;
(106) ALGA0097282 the genotype of SNP site is TT;
(107) ASGA0079089 the genotype of SNP site is CC;
(108) INRA0055354 the genotype of SNP site is GG;
(109) ASGA0079091 the genotype of SNP site is TT;
(110) ASGA0079090 the genotype of SNP site is CC;
(111) H3GA0050491 the genotype of SNP site is AA;
(112) MARC0056017 the genotype of SNP site is TT;
(113) MARC0055759 the genotype of SNP site is AA;
(114) H3GA0050495 the genotype of SNP site is GG;
(115) ALGA0097291 the genotype of SNP site is GG;
(116) ALGA0097290 the genotype of SNP site is GG;
(117) CASI0006683 the genotype of SNP site is GG;
(118) ASGA0079098 the genotype of SNP site is CC;
(119) ALGA0097297 the genotype of SNP site is GG;
(120) H3GA0054426 the genotype of SNP site is TT;
(121) ALGA0098112 the genotype of SNP site is GG;
(122) MARC0089391 the genotype of SNP site is GG;
(123) ASGA0089892 the genotype of SNP site is AA;
(124) ASGA0097792 the genotype of SNP site is CC;
(125) MARC0046857 the genotype of SNP site is GG;
(126) MARC0077194 the genotype of SNP site is AA;
(127) ALGA0108769 the genotype of SNP site is CC;
(128) H3GA0050799 the genotype of SNP site is CC;
(129) ALGA0098120 the genotype of SNP site is CC;
(130) ALGA0098123 the genotype of SNP site is GG;
(131) ALGA0098128 the genotype of SNP site is GG;
(132) ASGA0079719 the genotype of SNP site is CC;
(133) ASGA0079728 the genotype of SNP site is GG;
(134) ASGA0080429 the genotype of SNP site is CC;
(135) MARC0052755 the genotype of SNP site is GG;
(136) ALGA0098918 the genotype of SNP site is GG;
(137) ASGA0080432 the genotype of SNP site is GG;
(138) ALGA0098922 the genotype of SNP site is CC;
(139) INRA0056206 the genotype of SNP site is GG;
(140) INRA0056207 the genotype of SNP site is CC;
(141) ASGA0080435 the genotype of SNP site is CC;
(142) MARC0068495 the genotype of SNP site is GG;
(143) ASGA0080436 the genotype of SNP site is CC;
(144) MARC0003370 the genotype of SNP site is CC;
(145) ASGA0085659 the genotype of SNP site is CC;

If more than one of the samples to be tested do not satisfy all the standards of the above (1) to (145), the pig population to be tested is a candidate for non-Wuzhishan miniature pig inbred line population.

In the method, samples to be tested with statistic significance are obtained by randomly sampling from the pig population to be tested.

In the method, more than 16 pig samples to be tested are obtained by randomly sampling from the pig population to be tested.

The pig to be tested can be Wuzhishan miniature pig inbred line or Hainan Wuzhishan pig.

The Wuzhishan miniature pig inbred line can belong to any one of $F_{20}$ to $F_{22}$ generations.

The Wuzhishan miniature pig inbred line can belong to $F_{20}$ generation or generations later than $F_{20}$ generation.

In the method, specific chips can be employed to test genotypes based on 145 SNP sites of the pig to be tested; the specific chips are nucleic acid chips in which single-stranded DNA molecules shown as Sequences 1-145 in the sequence listing are immobilized at different points, respectively.

THE BEST MODE FOR CARRYING OUT THE INVENTION

The following examples are convenient for better understanding the present invention, but not to limit the present invention. Unless otherwise specified, the experimental methods in the following examples are all conventional methods. Unless otherwise specified, the experimental materials used in the following examples are all commercially available from conventional biochemical reagent stores. The experimental animals include 48 Wuzhishan miniature pigs inbred line, of which 16 for $F_{20}$ generation, 16 for $F_{21}$ generation, and 16 for $F_{22}$ generation, as well as 16 non-inbred line Hainan Wuzhishan pigs.

Wuzhishan Miniature Pig Inbred Line:

Li Kai, Feng Shutang, Mou Yulian, Yang Shulin, Han Jianlin, Liu Lan, Yuan Xinxu, Guo Yong, Study on Genetic Regulation of Microsatellite Loci Gene of Three Inbred Families of Wuzhishan Miniature Pig, Scientia Agricultura Sinica, 2012, 42 (5): 1751-1760.

Hainan Wuzhishan Pig:

Hou Guanyu, Wang Dongjin, Guan Song, Rong Guang, Huang Xianzhou, Detection of Genetic Quality of Small Population of Wuzhishan Pig, Acta Ecologiae Animalis Domastici, 2007, Volume 28, Issue 6: 44-47.

Example 1, the Establishment of the Method

The inventors of the present invention found that there are 145 SNP sites when genome researches are made on Wuzhishan miniature pig inbred line and non-Wuzhishan miniature pig inbred line, and Wuzhishan miniature pig inbred line and non-Wuzhishan miniature pig inbred line can be identified according to their genotypes. The genotypes of 145 SNP sites of Wuzhishan miniature pig inbred line are all homozygous types (genotypes described in Table 1). The genotypes of 145 SNP sites of non-Wuzhishan miniature pig inbred line are all heterozygous types.

In the 145 SNP sites, 12 SNP sites are located at first segment of chromosome 1, 16 SNP sites are located at 15th segment of chromosome 1, 14 SNP sites are located at 50th segment of chromosome 1, 16 SNP sites are located at 78th segment of chromosome 1, 15 SNP sites are located at second segment of chromosome 2, 14 SNP sites are located at 12th segment of chromosome 2, 13 SNP sites are located at 19th segment of chromosome 2, 20 SNP sites are located at fifth segment of chromosome 18, 13 SNP sites are located at 14th segment of chromosome 18, and 12 SNP sites are located at 20th segment of chromosome 18.

Based on 145 SNP sites, the inventors of the present invention designed 145 probes (the binding domain of probe with genomic DNA is adjacent to SNP site, and located upstream or downstream of SNP site, therefore, genotype of SNP site can be obtained via terminal extension).

As for names of 145 SNPs, their located chromosomes, their positions on the chromosomes, the genotypes of Wuzhishan miniature pig inbred line, source types of SNPs, nucleotide sequences of 145 probes, and source sequences of SNP on genomic DNA, see Table 1.

TABLE 1

| | chromosome | SNP name | the positions on the chromosomes | Genotype of Wuzhishan miniature pig inbred line | Source type of SNP | probe | Source sequence |
|---|---|---|---|---|---|---|---|
| 1st segment | 1 | M1GA0025062 | 2687123 | GG | [T/G] | TTTGGTCTAC AGAACGAGA GTCTCGCGTC GGGGTCTGAG CATCTTGCGT G | NCTGGAGACCTGCTGCA TTAACGGCATTCGGCCG GTGCTGGGCCTGGGCCT GCTCTGCCC[T/G]CACG CAAGATGCTCAGACCC CGACGCGAGACTCTCG TTCTGTAGACCAAAGA AATCTACA |
| | 1 | DRGA0017627 | 2737789 | GG | [A/G] | TCTGATACAA ACAAATTCCG ACTTGTGGAA TTGTAAATATT TGTCGATTC | CCTCATTTCTTCTGATAC AAACAAATTCCGACTT GTGGAATTGTAAATATT TGTCGATTC[A/G]TCTTT CTTTTAAAGNNNNNNNN NNNNNNNNNNNNNNNN NNNNNNNNNNNNNNNN NNNNNN |
| | 1 | H3GA0056137 | 2760895 | CC | [T/C] | TGGTGTTGGC TGCGCGTGGG AGGGAGGTAT CTTAGAAGCA AACGGGATAA | NNNNNNNNNNNNNNNCT GCGAACTACTCTTAAGC AGAACAGGGAGGGGCC AAGTCCAAGAG[T/C]TTA TCCCGTTTGCTTCTAA GATACCTCCCTCCCAC GCGCAGCCAACACCAC GGGGAAGCG |
| | 1 | MARC0039661 | 2780208 | AA | [A/C] | ACCAGGGGAC AAAGGAAACC TGTTTCCTACC GTTCCATTACG TCAGTGTG | TCTGGTGCACACCAGG GGACAAAGGAAACCTG TTTCCTACCGTTCCATT ACGTCAGTGTG[A/C]AA TTAACAAACACCTGAAA ACATCACAGAATCCTTTT GAGTAAGAAAACCCAA AACTTNN |
| | 1 | ASGA0085025 | 2788885 | TT | [T/C] | ACAACAAAAA AGAAAGCAG GCCAAAAAAG AGTTCACACT CTACAAGGCC A | AGACCAAAAAACAACA AAAAGAAAGCAGGCC AAAAAAGAGTTCACAC TCTACAAGGCCA[T/C]G TAGGCAAAAATCCTAGA AAATGCAGCTGAGACAC GCAAGGGGATAGGCAA GGCACACA |
| | 1 | ASGA0098570 | 2789574 | GG | [A/G] | CGAATCGAAG AAAATACAGA CTCTCTGTAGT TCCAGCACCA | NNNNNNNNNNNNNNNN NNNNNNNNNNNNNNCT GGAAGGCATGTATCTAAT CGTTAATGGT[A/G]CTTC |

TABLE 1-continued

| | SNP chromosomename | the positions on the chromosomes | Genotype of Wuzhishan miniature pig inbred line | Source type of SNP | probe | Source sequence |
|---|---|---|---|---|---|---|
| | | | | | AAGGAGAAG | TCCTTTGGTGCTGGAA CTACAGAGAGTCTGTA TTTTCTTCGATTCGCCT TTTTGTA |
| | 1 | MARC0063358 | 2829500 | AA | [A/G] | CTGCTTTACTC AGTCCTTCTT GTGTCGCGTC TGTCATCGTT GTGTAGCTC | CTGACTCCAGGCACCGG GATAAGAGCAGCTCTGT TGTCACAGAACTTGTCA TCTACCGGA[A/G]GAGC TACACAACGATGACAG ACGCGACACAAGAAGG ACTGAGTAAAGCAGAA GGAACAAG |
| | 1 | ASGA0085437 | 2835242 | GG | [A/G] | TCGTCGTAAG ACTGTCGCAA GACTGTCGCA GTGTCGCAGT GACAGCACCC | CGTCGGGCCCTCGTCGT AAGACTGTCGCAAGAC TGTCGCAGTGTCGCAG TGACAGCACCC[A/G]GG GAGNNNNNNNNNNNNN NNNNNNNNNNNNNNNN NNNNNNNNNNNNNNNN NNNNNNNNNN |
| | 1 | MARC0096709 | 2840543 | CC | [T/C] | CCCACTGAGC AGACAAATCA GCCTTAAACA CTGCTGACCT TAAACATCAG | AAAAGAAGCTCCCACT GAGCAGACAAATCAGC CTTAAACACTGCTGAC CTTAAACATCAG[T/C]T CGATATTCTAATATTTTCT TTAACCACATGCACTTTT AGGAGTAATACACCCAT GCACT |
| | 1 | H3GA0052387 | 2908940 | GG | [T/G] | GGGTCCCCAG CAGCGTCTTT TTATTTGTATT AGTGGTGTCT GCCAACAAG | ACGTGGCTCGGGTCC CCAGCAGCGTCTTTTT ATTTGTATTAGTGGTGT CTGCCAACAAG[T/G]GG CCAACGTGTCGCCACTG GCACTTCTGATGACACG CACAAGTTGGTTCCCAC TGCTGTG |
| | 1 | ASGA0000264 | 2950020 | TT | [T/C] | GGCTGGAGGA ACATGGATTT GGAAGCAGA AGCTCGGATG GAGATGCAGA G | GGGCCTTCTGCCACAGC ACTGCCACGCCCCCCAC AGGCGCCCTGCTGTCCA GCTTGGGCG[T/C]CTCT GCATCTCCATCCGAGC TTCTGCTTCCAAATCCA TGTTCCTCCAGCCCCG GGTCCC |
| | 1 | ALGA0000195 | 2965787 | TT | [T/C] | CTCTTCCAGG TAAGATTCATT TACACCGAAT CCATTTTCCGC AGCTTAGC | GTGTCCGCGCCAACTCA CGATTCGCTATTGATCAG GTGTCTCACGGCTCTGC GGGGCAGA[T/C]GCTAA GCTGCGGAAAATGGAT TCGGTGTAAATGAATC TTACCTGGAAGAGATG CTGACGA |
| 15th segment | 1 | H3GA0001444 | 38635057 | AA | [A/G] | GGTATCCCTTT AATATAGGCG TTCCTAACCT GGATGTTTTT GAGTTGAAC | GAGACTACAAGGTATCC CTTTAATATAGGCGTTC CTAACCTGGAGTTTTT GAGTTGAAC[A/G]TAGG CCACTGGAGAATTTGTA CGTGAAAAAATTCTAT CTTACTTCCACTAATTTC CAGT |
| | 1 | ASGA0002293 | 38700672 | CC | [T/C] | GGCCATGCCT GCAGCATATG GAAGTTCTTG GACCAGGTAT TGAGATCTGA | GTAGCAAAGTGGGTTAA GGATCTGGTAATGCTGC AGCTGTGGCATATGTCCC AGCTGAGG[T/C]TCAGA TCTCAATACCTGGTCC |

TABLE 1-continued

| chromosome name | SNP | the positions on the chromosomes | Genotype of Wuzhishan miniature pig inbred line | Source type of SNP | probe | Source sequence |
|---|---|---|---|---|---|---|
| | | | | | | AAGAACTTCCATATGC TGCAGGCATGGCCAAA AAAGGAA |
| 1 | INRA0001752 | 38719724 | GG | [A/G] | TAGGTAGATA GATAGACAGA TAGTTAGATAG CAGACAATAG ATACAGAAA | ATTTTATCTGTAGGTAGA TAGATAGACAGATAGTT AGATAGCAGACAATAG ATACAGAAA[A/G]ATGG TGAAAAACCCTATCAAA ATTAGAAGGAAAAGAAG TGAAAAATATGATTCAT TCCA |
| 1 | H3GA0001445 | 38742311 | GG | [A/G] | TGGGAATACA CAAAAGAATT AAATCAACAC CTTTCACAAT CACAGGCCAA | TTAACCACTGCGCCACG ACGGGAACTCCATCAGC TTATTTATTCTTTAGATAA ACCCAGA[A/G]TTGGCC TGTGATTGTGAAAGGT GTTGATTTAATTCTTTT GTGTATTCCCATCCTGA GAAT |
| 1 | ALGA0002595 | 38758520 | TT | [T/C] | TCAAGAAGAA TTTCTAGCTG AGATGAAAAG AGTTCTCCTC CAAAGTAAAA | ATGTTCAGATGTTCACAA TTTCCATGTGAAAAGTTT ACTATGGCTTATAGTGAA TGACAT[T/C]TTTTACTT TGGAGGAGAACTCTTT TCATCTCAGCTAGAAA TTCTTCTTGAACTTGAT CTC |
| 1 | ALGA0002600 | 38781031 | GG | [A/G] | GATATACAGTA GGAAAGATAT GTCAGCTCCC TCTCCCTCAC ATAACTAAC | GGCAGAAGTTGTTTTGT ACATCATTGGATCAATTG AAAAATTGTCCACAGAT AACTGAAT[A/G]GTTAG TTATGTGAGGGAGAGG GAGCTGACATATCTTT CCTACTGTATATCATAC TCAGAA |
| 1 | DRGA0000563 | 38827035 | CC | [A/C] | GATTCTGAAC TTGAAACTCT CACTTCTTCCT AAGATAAGCA AACTACATG | AGCATGTTAGCATCACAT AGAAAGAACAACATGA AAAGAGAATTTTAAATT GGTCTTTGR[A/C]CATGT AGTTTGCTTATCTTAGG AAGAAGTGAGAGTTTC AAGTTCAGAATCATTTC AGTTT |
| 1 | DRGA0000565 | 38844193 | CC | [T/C] | GGAGTCATAT GTCTATCAGTA AAGAGTCAGC TAATACTTTAA ACTTTGCC | AAGGGCTAGAGGAGTC ATATGTCTATCAGTAAA GAGTCAGCTAATACTTT AAACTTTGCC[T/C]GCC ATTGGTCATTACCTTTGT TGTTAGACCTTCCTTAAA GAATGGCTAAAGGTAGT TCTT |
| 1 | INRA0001761 | 38870043 | AA | [A/G] | TTCTGGCACA AATGTGCTAC TTTTATATCTT TTTCCCATTTT AAAACTTT | TTTTATGTGATTCTGGC ACAAATGTGCTACTTTT ATATCTTTTTCCCATTT TAAAACTTT[A/G]CATTT GTATTTGTTTGTTGTTAT TTAATAATTCTTTATATAA TTAGGATATTTACATTCC |
| 1 | MARC0104045 | 38873519 | CC | [T/C] | GAGCCACAAT GGTAACTCCT CTTATAGCAAT TTTAAATACC ATGAAAAT | TTCCAAAAAATACTTAA AAACTCGCCTCCCCCAA ATATTACTTTTCCAAAAA AGAAAAAA[T/C]ATTTT CATGGTATTTAAAAATT |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | | | | | | GCTATAAGAGGAGTTACCATTGTGGCTCAGCA GTAACA |
| | 1 | ALGA0002601 | 38889713 | CC | [T/C] | CTTCCTTTTTC CTTTTCAAGA GCTTTGCTGC CCAAGACAGG AATCCAGAG | CTGAGAATTCTCTCATTG CACCCCACCTTGGTGAA GCTCATCAAGCACGGGA GATGATCA[T/C]CTCTGG ATTCCTGTCTTGGGCA GCAAAGCTCTTGAAAA GGAAAAAGGAAGGAGT TCCCGT |
| | 1 | DRGA0000569 | 38910676 | AA | [A/G] | TTGGTCTTTTT TGTAGCCTTC CTTTTTTCTGC CTTTTAAATAC TGTGGTG | ATTACCTGTTACTTTTAA GATAAAAATTTACATTTG AAACCCAAGACAAATAC TGTGAAA[A/G]CACCAC AGTATTTAAAAGGCAG AAAAAAGGAAGGCTAC AAAAAAGACCAAGCTG GGGCAA |
| | 1 | ALGA0002608 | 38931921 | TT | [T/G] | AGGGGAAGA CATGGTTGTG GCTTGACCTT GGAAAGATGA GCTAAAGGTG C | AAATCCCAGCAGGGGA AGACATGGTTGTGGCT TGACCTTGGAAAGATG AGCTAAAGGTGC[T/G]G AGGAAACCATAAATTCA ATTTGCAATAATAACAAA AATAAATGTTGTTACAC TTTGCC |
| | 1 | DRGA0000568 | 38946998 | CC | [T/C] | ATCACATACAT ACTGAAAAGT GATGGAACAT ATCTTGAAAC CAATTTGAC | GCAGTATATCATCACATA CATACTGAAAAGTGAT GGAACATATCTTGAAA CCAATTTGAC[T/C]TAGT AACTTCATATTTAAACAT AATTAGAAACACAAAGA TTTATTTATCCCATTAATT GA |
| | 1 | ALGA0002604 | 38953492 | GG | [A/G] | CAGTAAAGTG CTTCAGAGCT TTGGTAATTTG GGCATCCTTGT ATCACCTT | GTTTTGCTGTCAGTAAA GTGCTTCAGAGCTTTG GTAATTTGGGCATCCT TGTATCACCTT[A/G]ATT GTACTCTCATGTTAATGA AGTCAGCAACAAACATC TTACAGTATAATCTCTTA CATA |
| | 1 | MARC0048118 | 39019040 | TT | [T/C] | CAATGGAGGT AATAAGAAAT GGTTAGTTCTA TATGTACTTTG AGTGCAAA | TAYAAAGATTCTTYATTG AAAGTAGGKGGGAAAA ACACAACCCAAAAGAA ATATTTTTGG[T/C]TTTG CACTCAAAGTACATATA GAACTAACCATTTCTTA TTACCTCCATTGCTGCC GCATC |
| 50th segment | 1 | ASGA0004229 | 120634567 | CC | [T/C] | AAGGCACTTC ATAGTTAATAG CTATTAGAATC CTAGAGCTGC ATAGAGAA | CAGCCAAAATAAGGCA CTTCATAGTTAATAGCT ATTAGAATCCTAGAGCT GCATAGAGAA[T/C]ATA AATCCACAGGAACTTTA AGCTCACTCTCCTCTCTT GTCTTTTATTAGAGAATC TACA |
| | 1 | MARC0007088 | 120722033 | CC | [T/C] | AACAGTCCAC CAGACAAGCC TCTGAAAGCC CAGGGCACAG CCACCACTGT | TCACAGGTGAGGAAGG GAGGCTGCAGGGCTCAC GACTTTAGCCACACACC TTGTGTGAGG[T/C]ACA GTGGTGGCTGTGCCCT GGGCTTTCAGAGGCTT |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | | | | | | GTCTGGTGGACTGTTCCCCATAAGT |
| 1 | MARC0000061 | 120816036 | GG | [A/G] | AAGACGTGATGCAGCAAGCTCTGTGATGTAACAGGTACCCCACTCTGCTG | GCTGTTGGGAAAGACGTGATGCAGCAAGCTCTGTGATGTAACAGGTACCCCACTCTGCTG[A/G]CTTTTGGGCTTCGGTGATTGGCTGCTACCTGCTTATAAGGTGAACAAAAGATATTTGCTG |
| 1 | MARC0094747 | 120855165 | AA | [A/G] | TTCAGATCTCAGTCTGGACAGGGCAGTGTGTTCTTTTTATGATAATGGGC | ACAAGAGCCTTTCAGATCTCAGTCTGGACAGGGCAGTGTGTTCTTTTTATGATAATGGGC[A/G]CTGAGGCTCAGAGGTGGACATTTGTATAACTCTTGAGGTCATTGGTGTCATTGGACAGGG |
| 1 | MARC0007969 | 120894943 | AA | [A/G] | CTGAGGATGGTTTTATGCCAAGAGACTCCACAGTCAGCTTAATAACCTTA | TTTTTGCCTCCTGAGGATGGTTTTATGCCAAGAGACTCCACAGTCAGCTTAATAACCTTA[A/G]GCGACTCATGATTGAGAAGATACGTTTATTGTTGAAAACTGTAAAAACAGAATACATTCC |
| 1 | ASGA0106092 | 120908439 | CC | [A/C] | AAATGGTTCTGACCCAAAAGAGAGGACTGTTCTAAGCAACCATGTGCAGG | NNNNNNNNNNNNNNNNNNNNNNNNNNNNNNNNNNNNNNNNCTGGTGCCCTGTCTGGCCAAT[A/C]CCTGCACATGGTTGCTTAGAACAGTCCTCTCTTTTGGGTCAGAACCATTTCCAGTGCAAG |
| 1 | ALGA0119806 | 120951068 | GG | [A/G] | TGGACTTCCCAATGCCTGCCTTGTCTCTCCTATCCCAGAATCCCTCAGTG | NNNNNNNNNNNNNNNNNNNNNNNNNNNNNNNNNNNNNNNNNCTGTATGGTCA[A/G]CACTGAGGGATTCTGGGATAGGAGAGACAAGGCAGGCATTGGGAAGTCCAGGGGTCGAGA |
| 1 | INRA0003745 | 121128221 | AA | [A/G] | ACTGCAGCAATAAGTGCAACTGTCACTTTGTTCTGTGGAAAATGCCCTGG | TTCCCAGAGCAGACTCGTTGGACTCAAGACTCGTTGGACTCAGGATGAGTTCTCATAACC[A/G]CCAGGGCATTTTCCACAGAACAAAGTGACAGTTGCACTTATTGCTGCAGTTTCCCAACAA |
| 1 | INRA0003746 | 121128357 | TT | [T/C] | CATTTGTTCTTTGGGGAAAAGATTGGACAGAAGAGATCCATGTTTTCTCC | TTGCCTAACATGCAATCATTAGAACTTATTGCCTTGGATCTAAGGCTTTTCACTGCTTC[T/C]GGAGAAAACATGGATCTCTTCTGTCCAATCTTTTCCCCAAAGAACAAATGAGAGATGAGT |
| 1 | ALGA0005490 | 121307042 | CC | [A/C] | TCTCTTGCACAAGGGGATATTCTATTGAATTAATGGCCCTGGAAGGACAA | TGGTATTCCATCTCTTGCACAAGGGGATATTCTATTGAATTAATGGCCCTGGAAGGACAA[A/C]AGGTAGCCATGACCCACCA |

TABLE 1-continued

| chromosome | name | SNP | the positions on the chromosomes | Genotype of Wuzhishan miniature pig inbred line | Source type of SNP | probe | Source sequence |
|---|---|---|---|---|---|---|---|
| | | | | | | | GCCATGGAGCTGTCCAC CCTGGAAGCACCCTCTT AGTCAGG |
| | 1 | H3GA0002538 | 121356509 | CC | [A/C] | CACATTAAGC CTTATGTTTTA CTTACCTCGG AAGCATGAGC CATGTGATA | CCTCTGTGACCACATTA AGCCTTATGTTTTACTT ACCTCGGAAGCATGAG CCATGTGATA[A/C]CTG GGAGGATGGTGTAACAG GATGAGGCCCTGTGCCT GGAACACCCAAATCTAC CCAGAG |
| | 1 | INRA0003749 | 121441133 | CC | [T/C] | ATCTGAATAC AGCCAACGTT CAGTGATACC ACACCATCCA CTTTGGACAT | AGTTTTTCATTTTAACTT GGATTTGTATCCAGATGC TACTGAGGGGGATTCCT AYACTGA[T/C]ATGTCCA AAGTGGATGGTGTGGT ATCACTGAACGTTGGC TGTATTCAGATTGTCTA TCTC |
| | 1 | H3GA0002539 | 121478005 | GG | [T/G] | ATCAATTTGTA CCACGAGTGA GTTGGAATGA CTGGCATTAG GATTCGACA | CATGGATATACAGAAGTT GCAAAAGTCCCTGTGGC CAGACCTGGACGGCGGC TATATAAT[T/G]TGTCGA ATCCTAATGCCAGTCAT TCCAACTCACTCGTGG TACAAATTGATGCAACT GAAG |
| | 1 | M1GA0001099 | 121626075 | CC | [T/C] | AAACTCACCA GGGCAACATC TTCCATGAAG CTCATGTAACT TTAATGCCT | ATTCGGAAGTAAACTCA CCAGGGCAACATCTTC CATGAAGCTCATGTAA CTTTAATGCCT[T/C]GTC CTGGCATTGTTTCCCCA GCCGGTACTGGCCCCTC TGCGTGGCCTCCTGGAG GCCAGG |
| 78th segment | 1 | MARC0111831 | 225656477 | AA | [A/C] | AAATACCTTC CCGTTCTCCC ATTTCTAATAT AAGACAGGGA TGAGGATAC | CCTAGGCAACAAATACC TTCCCGTTCTCCCATTT CTAATATAAGACAGGG ATGAGGATAC[A/C]NKK WAAANNNNANNNNNNT TTTAAAANGCCCANGAN GNCTTTCTTTTATTGAAG TATATT |
| | 1 | ASGA0005566 | 225713764 | CC | [T/C] | AATATGACTG AGTTAGGTAC TTGGAGGGTG AAGGATAAAA AAGATACAGA | ACTTCAAAATAATATGA CTGAGTTAGGTACTTG GAGGGTGAAGGATAAA AAAGATACAGA[T/C]TA GCTATGGAATGATAACCA TTAAGGAAGAGATATCTA TAACAATTTACTACATCT TCAA |
| | 1 | ALGA0007578 | 225761304 | CC | [A/C] | CTTGGGTGCT CTTGAAAATC CCAATTCAATT CAAACCCAGC TGTTCTGAT | ATAGGAAGGACTTGGG TGCTCTTGAAAATCCC AATTCAATTCAAACCC AGCTGTTCTGAT[A/C]A AAATTCTGGAGTTAGTA CTAAGGATATGGTCCTGC TCACAGACACACTGGCA TTTCCCA |
| | 1 | ASGA0005568 | 225825860 | CC | [T/C] | TGATCTGGCA TTTGAGGACT GTTGTATCAGT TTGAAAGTAA GACAGCTTG | TCAACTTCAGACTACTTT TGGCCCTCAGTCCAAAT TCAAACCCTATTTGTGA AATTGCTC[T/C]CAAGCT GTCTTACTTTCAAACT GATACAACAGTCCTCA |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | | | | | | AATGCCAGATCAGCTCC AGAGC |
| 1 | INRA0005765 | 225854493 | AA | [A/G] | CCCTCCCCCTA TATATATTTAA AATATAGATGT TGCTTAATATC AGAACA | CTCCCAATGATAATAAGC AGTTACCAAGAGCTAAC TGTTGTTTTCATATTTCTA TTTTTT[A/G]TGTTCTGA TATTAAGCAACATCTAT ATTTTAAATATATATAG GGGGAGGGTTTTCTGT CT |
| 1 | MARC0095347 | 225889929 | CC | [A/C] | TAGAGTTTGT GCCAATCTGG TTGTGCCACA GCAGGGACTC CCTGTACACA | ATCTCTCAACTTTTTCCT TCAATCAAGACTTAATTC TCTTATGCAAACCCACAT TTAAAA[A/C]TGTGTAC AGGGAGTCCCTGCTGT GGCACAACCAGATTGG CACAAACTCTAGAGGC TGAGA |
| 1 | MARC0039015 | 225944274 | CC | [T/C] | TGACTAAATA AGGTTTGTTC CAAATATTACA GGGCATAATG AAAAAGATC | CCCAGATTACTAATCAGT [T/C]GATCTTTTTCATTA TGCCCTGTAATATTTGG AACAAACCTTATTTAGT CAGAGTGCTTCA |
| 1 | DRGA0001892 | 225986595 | GG | [A/G] | TTAAGTACTT GCCAAAGAAT TAAAATAAAG ATAAGCAATG CTTTAAAAAA | GGAATCCTAATTAAGTA CTTGCCAAAGAATTAA AATAAAGATAAGCAAT GCTTTAAAAAA[A/G]AT AGAAAGAAAACAAATG AATACAAAGTTGAAAGG AAATTGTATTTGAAAAA GCAACTGA |
| 1 | ALGA0007580 | 226149776 | GG | [T/G] | GCTCATTCATC CAACACATAC ACAGGCTA ATCAGAAGCA AACACCCAC | GAATGTATGCTTACATAC AGTCGTATCAGATGGAA GAAGCTAGTTTCTAAAA CAGTTCGG[T/G]GTGGG TGTTTGCTTCTGATTAG CCTGTGTGTATGTGTT GGATGAATGAGCAATT GGGAAG |
| 1 | ALGA0007583 | 226188042 | TT | [T/C] | AGGAAAATTC CCTGCCTAAA GCCACATAGC ATCATCTTAGG AAATAAACC | TATCAAGGGAAGGAAAA TTCCCTGCCTAAAGCC ACATAGCATCATCTTAG GAAATAAACC[T/C]GGG GCTTCTTATTCCCAGCTG ACTGTTTTCTTTGAGATC ATTGAAAAATATATATAA TTG |
| 1 | MARC0095915 | 226237014 | CC | [T/C] | GCTACAGATG TATACGTAGAT TCTTATAACTG TCCAATGAAC TAAGTGTC | GCAAAGTTATGCTACAG ATGTATACGTAGATTCT TATAACTGTCCAATGAA CTAAGTGTC[T/C]AACA TGAAAGATGTTTGGTTA AATGTTAGATTTAATTG ACAAAAAACCATACAGA TGTT |
| 1 | ASGA0005571 | 226278675 | AA | [A/G] | CCATGTAGTTT TCAGTCCACT GTGAAATTTT AACCTTTTTC GTATGTCTA | TCACACATTGCCATGTA GTTTTCAGTCCACTGT GAAATTTTAACCTTTTT CGTATGTCTA[A/G]CCA ATCTGGTATCCCAGCTTT GGAGGTGGGGGTATTCA GAGAAGTGGGCATCTGA TTCAA |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | 1 | MARC0014134 | 226300834 | AA | [A/G] | CAATCATTTCA TATACCAGTGT GCAAATATAAT ATGCAAGACC AAAAAA | CCAATCATTTCATATAC CAGTGTGCAAATATAAT ATGCAAGACCAAAAAA A[A/G]KWACATATTGAGT CTCTATTATGCCATATGC CGTGTACCATATATTACT TCATTNAANNN |
| | 1 | MARC0024233 | 226319468 | AA | [A/C] | AACCTGTTTC ACTCTTGTCG ATGCAGCCAA GTGGCAGGGA AGTCCTCAGC | AGTGTTTTGTAACCTGT TTCACTCTTGTCGATG CAGCCAAGTGGCAGG GAAGTCCTCAGC[A/C]A ATTTGTGCCTTGGGAAA TGG |
| | 1 | H3GA0003548 | 226335313 | GG | [A/G] | AGCTTAACAG GTGGCTCTGG AGGAAACACA CTTGGTCTGA GATATCACGG | AGAGGGGAGAAGCTTA ACAGGTGGCTCTGGAG GAAACACACTTGGTCT GAGATATCACGG[A/G]G GCCTCCTCTTGGCTTGTT GCAAGGACTTGACTTTC CTTCTGTGTAAGACAGG AAGCCTT |
| | 1 | ALGA0007591 | 226408018 | CC | [T/C] | ATAAAAAATG AGTTGGTGAG TTTGTACAAG TCACTCAGCT ACCCAGTGTG | AGCAGTAGAAAAAGCA CCAAAACAGGAGAGTC AGAGAACAGGGTGTCA GTTCCATTCTTA[T/C]CA CACTGGGTAGCTGAGT GACTTGTACAAACTCA CCAACTCATTTTTATC ATGTAGGAA |
| 2nd segment | 7 | MARC0000195 | 12606764 | CC | [T/C] | GGAAGCCAAT ATGTAAGATA GTAAGGTGAC TCATCTTTCAT TGGTGCAGC | AAATATGGGCTTCTTGG GATAACATTCACGAAGA TGCTGAAGGAAGGCTTC AGCATGCTT[T/C]GCTGC ACCAATGAAAGATGAG TCACCTTACTATCTTAC ATATTGGCTTCCTCTTC AAAAT |
| | 7 | ALGA0038697 | 12641640 | CC | [T/C] | CAAAGGGTCC TTTCTCCCCA GTAGAGCCCC TAATGAAGAA ATGTTCTTGG | CCTGTGTCCTGCTCAGC ACATGACTTTTGGTGTG TCGACTTCAGAGCTGCG TGGGATGGA[T/C]CCAA GAACATTTCTTCATTAG GGGCTCTACTGGGGAG AAAGGACCCTTTGACA GTTAAGA |
| | 7 | H3GA0020000 | 12679908 | CC | [T/C] | CAGTAACAAA TTACCACAAA CTTGGTGGCT TGTAACAATA GAACCGTGTT | CCTAAGGCTACAGTAAC AAATTACCACAAACTT GGTGGCTTGTAACAAT AGAACCGTGTT[T/C]TC TCATTCTTTTGGAGGCC AGAAGTCTAAAATTTTA TCACTGGGCTAAAATCA AGGGTC |
| | 7 | ALGA0038703 | 12710295 | CC | [T/C] | ACAAATATCTC ATGCTCATCTT GAGCCCTCGT ATGTGAGGCA AAGTGTGG | ATCACAGCCTACAAATA TCTCATGCTCATCTTGA GCCCTCGTATGTGAGG CAAAGTGTGG[T/C]GCC CAGGTGTCTTTGAATAG CTATATAATTAAGGTTTCT ATTTTTAAATCTACCTT CAT |
| | 7 | H3GA0020002 | 12731286 | GG | [A/G] | AATATTACAAC TAGTTTGACTT GCTAAGTGAG | TGTTGACTGATTACTTGT GATTCTTTTTTTTTTTTT TTTTTACTGCCTGTACT |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | | | | | AGCCAATCCA CAAGGCCC | CCCTT[A/G]GGGCCTTG TGGATTGGCTCTCACT TAGCAAGTCAAACTAG TTGTAATATTACTACAA CCA |
| 7 | DRGA0007138 | 12743235 | CC | [T/C] | TTCCTTATATA AAACAGTATA GTATCTGCATA TAACCTATACA CGTCCTC | AATGTTCAGTTCCTTA TATAAAACAGTATAGTA TCTGCATATAACCTATA CACGTCCTC[T/C]TATAT ACTTTAAATAATCCTAGA TTACTTGTAATACCTGAT AGAATATAGTGCGAATAT G |
| 7 | ASGA0031284 | 12781950 | CC | [T/C] | TCCAAGTCTC AGCCGACTTG GGAAATGGAA ATCCCCAGAT GATACCTCAG | GGCTTTTCTCTACTTTAA AGGCTAGAAAGCTATAA ACTACATTTCCCAGACT GCCTTGTA[T/C]CTGAG GTATCATCTGGGGATTT CCATTTCCCAAGTCGG CTGAGACTTGGAGGGT AGAAAT |
| 7 | ASGA0031285 | 12812114 | AA | [A/G] | GGTGAGTCAC TCAAATGAGA ACAAAGGAGC AGGATGGGTG GAGCTAGGAG | GAGCTGAAGTGGTGAG TCACTCAAATGAGAAC AAAGGAGCAGGATGGG TGGAGCTAGGAG[A/G]C AGCAAAGAGGAGCTGG AACTTCCCAGCTTGCGG GTCAGGACCCAGCAAG GAAGGGACTC |
| 7 | MARC0025042 | 12829776 | GG | [A/G] | ACACATCACA GAAGGGAGA AATGGAGATAT AGGATGAGGA CCTGAACCCC | CTGTTAGCTGAAATCTTA GTTTTTAGACTATGTAAT GTGGAATTCATCAGTTA AGAGGGA[A/G]GGGGT TCAGGTCCTCATCCTAT ATCTCCATTTCTCCCTT CTGTGATGTGTAAGGAT AAGS |
| 7 | H3GA0020006 | 12871039 | TT | [T/C] | AAAGTAACTG CCGAAGGACA TGAACTAATG AAAGAAATAA AAAGGGCCCC | ACACTGGCATCTGCATTT AAATTTGATGACTGGCA ATGTTGAATACTTTTCCT GTGTTTT[T/C]GGGGCC CTTTTTATTTCTTTCAT TAGTTCATGTCCTTCG GCAGTTACTTTATGAGG TGTT |
| 7 | ALGA0038729 | 12891883 | CC | [T/C] | TTCTGGCCAC ATGTACAGTT CTGTGAGTCA TCCTGGCTGT GGCCAGTGAC | CTGTGTTGGTTTCTGGC CACATGTACAGTTCT GTGAGTCATCCTGGCTG TGGCCAGTGAC[T/C]GG CTTTGGGAGCTGGGTCC CATAGACCAGCCCCCAG GCCAGCCCAGGGTCTGG CTCATGG |
| 7 | ALGA0038731 | 12918213 | GG | [A/G] | TGCTTTGAAT CCCAACCATG CCATGACCAT TTTGTAGCTCA TTTCAACCT | TGGTTTTAGTTGCTTTG AATCCCAACCATGCCA TGACCATTTTGTAGCT CATTTCAACCT[A/G]AA GGAGGCGCTGTCACAAA GGCGTGGATGGAACCAC GCAAAGTCCTGGACAGA ACCGTTC |
| 7 | ASGA0031321 | 12984109 | GG | [A/G] | TTGATGATTG AAGTTTCCAG CTCGCTGACC ACTCTTTCTTC | TGATGAGAGCTTGATGA TTGAAGTTTCCAGCTC GCTGACCACTCTTTCT TCACCTCCCTC[A/G]CT |

TABLE 1-continued

| chromosomename | | SNP | the positions on the chromosomes | Genotype of Wuzhishan miniature pig inbred line | Source type of SNP | probe | Source sequence |
|---|---|---|---|---|---|---|---|
| | | | | | | ACCTCCCTC | CCTGCCTCCTCTGTTAGC ACAAATCCTGTCCTTGG TTTATGTCATTCCTTGCT CAGTG |
| | 7 | ASGA0031322 | 13023831 | GG | [A/G] | AAGAGAAAAT AGCAAACATG TCCAAAAGTA GATCATAAGC TCCCATGTCC | GTCTGGGGAAGAGGGG TTGGGGATGGGTAGATG AAACTAGGCTGTTGACA TGGGGTGATG[A/G]GGA CATGGGAGCTTATGAT CTACTTTTGGACATGTT TGCTATTTTCTCTTTTCT TTCTTTC |
| | 7 | ALGA0038747 | 13071251 | AA | [A/G] | TGTGGAGAAC AGTTTGGCAG CTCCTCAAAA GGTCAAACCT AAAGTCACCA | TGTACATGTTTTTGGTG TGAACGCTCACTTTCAA TTCTCTCGGGCAGAACG GCTGGGTC[A/G]TGGTG ACTTTAGGTTTGACCT TTGAGGAGCTGCCAA ACTGTTCTCCACAGTG GCTGCAC |
| 12th segment | 7 | ASGA0033095 | 43103102 | TT | [T/C] | CGCATAGGAA GGAAAGCCGA GGTGCGCAGG TTAACAGCCA GTCAGCTCTC | CTCCTGGGACTCCCTCA CCTGCCTGCAGCTACTC ACAGGTCAGCTAGGCGG CTCTGCTCC[T/C]GAGA GCTGACTGGCTGTTAA CCTGCGCACCTCGGCT TTCCTTCCTATGCGCTC TCATCCT |
| | 7 | ALGA0040854 | 43127838 | GG | [A/G] | TAGGGAATTAT CCAACCTAAG GTAGTCTATG GAGATGCCTG AATTTGTAG | CTCTAAAATACCACTGC ACACTTGGGGATCTCCA GAGCCATCTTCATTTCTA ATCAGCTG[A/G]CTACA AATTCAGGCATCTCCAT AGACTACCTTAGGTTG GATAATTCCCTAGAACA ATTCA |
| | 7 | ALGA0040856 | 43166101 | AA | [A/G] | TTAAACAGTT AATCATCTAG GTTTTATTTAT AGTACCATTTT CCAGCTTG | AATGGGAACTCCAAAAT AACTTTTTTAATAGAGT ATCTTGTGAAACTCTGTT GCTTTAA[A/G]CAAGCT GGAAAATGGTACTATA AATAAAACCTAGATGAT TAACTGTTTAAAGGATA TCTT |
| | 7 | ALGA0040857 | 43190587 | GG | [A/G] | ATGCCATAGG CACCGCAATA GCAGATCCCA GCCGTACCTG TGACTTAACA | CCAAGTTTAACCCCTGG CCTCCTTCAGTGGGTTA AGGATCTGACGTTGCCA CAAGCTGCA[A/G]TGTT AAGTCACAGGTACGGC TGGGATCTGCTATTGC GGTGCCTATGGCATAA GCTGCAGC |
| | 7 | ASGA0033096 | 43205140 | GG | [A/G] | AGGAGTATCA TGCCTGAATT ACACAGCTGA TAAATAGCAG GGATTCAGAG | CAGACTCTCTAGGAGTA TCATGCCTGAATTACA CAGCTGATAAATAGCA GGGATTCAGAG[A/G]AG AGCTGTTCTTGTGGTAC AACATTAACATACTTTGG TGCTTAACATTCTTTCCC ATTTT |
| | 7 | INRA0025180 | 43234940 | AA | [A/G] | AGCAAGGCAG GATGTGATGA GGAAGGAGCC AAGAAAAGTA GACTGCAGAC | TCCAGGAGGAAGCAAG GCAGGATGTGATGAGG AAGGAGCCAAGAAAAG TAGACTGCAGAC[A/G]G AGGTGTGATGCATCTCT |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | | | | | | GGTAGAAGATGGGGGAA AGCTGGCTGCCTCCCCT ACGGGATT |
| 7 | ALGA0040859 | 43342944 | CC | [A/C] | GCTTCCCTCA CGCTTTACAC CTGTCCCTAG CTGCTCCACT GGAGGAGGTG | GACTCTCCCAGCTTCCC TCACGCTTTACACCTG TCCCTAGCTGCTCCAC TGGAGGAGGTG[A/C]C CGAGGTCTAACACACAC ACACACACACACACACA CACACACACAGGAAGGT AGCACCAG |
| 7 | H3GA0021216 | 43380793 | CC | [A/C] | AATATGTTACA ATACAAGAAA AGGGGGAATC CGCAACTTGG ACATTGGCA | TTATCTTTCTAATATGTT ACAATACAAGAAAAGG GGGAATCCGCAACTTG GACATTGGCA[A/C]AAG TAAGGAAACCATGGCAA CCGTAAAACGGCCCAGA TTTTCCAATTTCTATTGG CTCGG |
| 7 | ASGA0033098 | 43400560 | CC | [T/C] | AGGTAAAGGT TTCTATTTGTC TCTGAGAAGT CAAGTTCCCT GTTAGCTAC | TTTATGGAAAAGGTAAA GGTTTCTATTTGTCTCT GAGAAGTCAAGTTCCC TGTTAGCTAC[T/C]CCCT TTCCCGAATTTGCATTTT AAGAAGGTGGCAGAGA AGACCAGATAGAACATT TGTAT |
| 7 | H3GA0021221 | 43423062 | CC | [A/C] | TATAGAATATT CCAATCTGGA AAATCTGGGA GTTCCTTGTT GGTCTAGTG | GATCTCAGTTCCCAGAC CAGGGATTGAACCTGGG CCAAAGCAATGAAAGCA GAATCTTAA[A/C]CACTA GACCAACAAGGAACTC CCAGATTTTCCAGATT GGAATATTCTATAACTA CAAACA |
| 7 | MARC0014540 | 43442829 | CC | [A/C] | ACCCTCTATAT TCCCTTGAAG TCTTATCTACG GAGACATCCT TTTGCTGT | GGGGTCAGGAGGGGTG GGAGGTGAGAAGGTTTC TGAGGCTCATGTCCTGG GAGAAAGAAT[A/C]ACA GCAAAAGGATGTCTCC GTAGATAAGACTTCAA GGGAATATAGAGGGTT CAGAGTTCT |
| 7 | ASGA0033103 | 43464853 | CC | [T/C] | ATGGAAGTTG CCAGGCTAGG GGTCCAATCA GAGCTGATGC CACCCAACTA | CCTGCGGCATATGGAAG TTGCCAGGCTAGGGGT CCAATCAGAGCTGATG CCACCCAACTA[T/C]GC CACAGCCACAGCAACGC CAGAGCCAAGCCTCATC TGCCACCTATACCACAG CTCATGG |
| 7 | DIAS0000557 | 43488849 | AA | [A/C] | ATGTTCTTTCC TGGGGTGCA CAGCCTGTGC TGAGGATGTG GTCGTAGTT | ACATCACAAGCATGGTG CGGTCAGGGGCTTGCT GGTCATTGATCATCG[A/C] AACTACGACCACATCC TCAGCACAGGCTGTGC ACCCCCAGGAAAGAAC ATCTACTATAAG |
| 7 | ASGA0033116 | 43505936 | AA | [A/G] | CATCAGAACT GCTGCACAGA TCTCCAATAG CTCCAGGAGG AAGAGTTTAA | TTGCTTTTCACTTGGCTT CTGACTGGCTGGGTTGC TGGGCTGCCTCTTCTGA CCTTCTCA[A/G]TTAAAC TCTTCCTCCTGGAGCT |

TABLE 1-continued

| | chromosome | SNP name | the positions on the chromosomes | Genotype of Wuzhishan miniature pig inbred line | Source type of SNP | probe | Source sequence |
|---|---|---|---|---|---|---|---|
| | | | | | | | ATTGGAGATCTGTGCAGCAGTTCTGATGCTGG ATTGTC |
| 19th segment | 7 | ASGA0036835 | 125807043 | CC | [T/C] | CTGCCAAGGA GACTGAGAGC TCTCAGGATTA TTGTATATTTG CCCAAGAC | TGCTATTGTACTGCCAA GGAGACTGAGAGCTCT CAGGATTATTGTATATT TGCCCAAGAC[T/C]CTAT AGAGAACTTGAACCCAT GTCTGTCTGAAGTCAAA GATCATATTTTGGCCATT ACGT |
| | 7 | MARC0031932 | 125822314 | CC | [T/C] | TAAAATTGCT GATTATTTTGA TCACTAATAAT GGTAATGCAA AGTCACTC | TATTCATTTAATAAAATA CTCTATAAGCACATAAAT AAATATGACTTCCTGATG TTATAT[T/C]GAGTGACT TGCATTACCATTATTA GTGATCAAAATAATCA GCAATTTTAATTACAGT TT |
| | 7 | ASGA0036838 | 125837557 | CC | [T/C] | ATCATGTAGTT AAATTCGTCC ACCCAGTGCA GGTTTCAGTAT CTACCAAA | CAGTCTGGTCATCATGT AGTTAAATTCGTCCAC CCAGTGCAGGTTTCAG TATCTACCAAA[T/C]AG CTCAAAGGATGTGAGCT GGAATTTTCTCCATAGCT CTTGGAGGGGAACTTTA GTTTGA |
| | 7 | H3GA0023523 | 125850169 | GG | [A/G] | ATTAACAGAA TGAAAGCCAA TCAGGGGAGG CCATGATTCTA GAGTGGCTA | TACTGAATGAATTAACA GAATGAAAGCCAATCA GGGGAGGCCATGATTC TAGAGTGGCTA[A/G]AG ACACCCAGCTCCCTCTG GTTCCTGTTTTCAAAAA GATCCAGTTTAGCTCCA GCTGCTG |
| | 7 | ALGA0045460 | 125871919 | TT | [T/C] | ATCCTATTTGC CAGTCTCACA CACTCACTGG AAGGAGCTAT AGAGGAAGT | CATATTGTGGTAGGCAG AAATCTAGGATGGCCCT CAGAATTCCTACCCCCC AGGGGTGAA[T/C]ACTT CCTCTATAGCTCCTTCC AGTGAGTGTGTGAGAC TGGCAAATAGGATGGA ATGTCAC |
| | 7 | MARC0005927 | 125942941 | GG | [A/G] | CAGGTCCTAC TGATGCAAAC CTTCAACTTAT AACTAACCAG TGACCTAAT | CAAGAGTGGACAGGTC CTACTGATGCAAACCT TCAACTTATAACTAACC AGTGACCTAAT[A/G]GA TCAATTCCAGAAAGATG TTAAGTGCAGGTGAGAG AAGAGGATTTGGGAAGA AAAATTM |
| | 7 | MARC0005928 | 125943001 | AA | [A/C] | CAGAAAGATG TTAAGTGCAG GTGAGAGAAG AGGATTTGGG AAGAAAAATT | RGATCAATTCCAGAAAG ATGTTAAGTGCAGGTG AGAGAAGAGGATTTGG GAAGAAAAATT[A/C]AA TTTCTGCATAACAAA AGATCCAGTACTTTGAA ACATCCTCTGTCTAGGG AAGGATA |
| | 7 | ASGA0036842 | 125986792 | CC | [T/C] | AATATGGACAT GAGGTTGGCA GGAGAGCTAT TCTACTGTGG GAACTGTCT | TGGGGAAAACAATCACA AAAATTCTCCTAAGGTC ATAAATGAGTAGTCATTA TTCTGAAG[T/C]AGACA GTTCCCACAGTAGAAT AGCTCTCCTGCCAACC |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | | | | | | TCATGTCCATATTCAGC TGAAAT |
| 7 | ASGA0036846 | 126014404 | CC | [T/C] | GGATGAACAA TATTGTGTGTA CGTACTGGAG AAGATTAACC CCAGCTACT | TTAAGCAAGAAATAAAC TTCAGAAGTGTTAACGC ACTAGAAGTTGAGGGTT TATTTRTTT[T/C]AGTAG CTGGGGTTAATCTTCT CCAGTACGTACACACA ATATTGTTCATCCATTT GCAAAT |
| 7 | MARC0098637 | 126028158 | TT | [T/C] | CACATGAAAT GAACTTTTAA ATAAAATGGTA TTTCCTACAAT GAGTTCCA | AAGCTGAAAGCACATG AAATGAACTTTTAAATA AAATGGTATTTCCTACA ATGAGTTCCA[T/C]GAC TTTTTGGGMGATGTTGG GTCAAGAAGGGAGTTTC GTATCCTAATATTTTGG GAGTA |
| 7 | M1GA0011035 | 126040140 | TT | [T/C] | GATTTGATGCT ATGCCCGGGC ATTGAAATTTC TTTAGAAACT AATGATAT | GCTGCTCTGAGATTTGA TGCTATGCCCGGGCAT TGAAATTTCTTTAGAAA CTAATGATAT[T/C]CTTA AGATTTTTCTCAGACTCT CTCCTTCAGTCCCAGGT TGAAGAGGGTCCTTCAA AAGT |
| 7 | DRGA0008230 | 126067443 | GG | [T/G] | AATTAAAGCA AAGGCATTAG TAAGAGTTTA AAAGGTTTGT GCTACAAAGT | TATAGTAAAAAATTAAA GCAAAGGCATTAGTAA GAGTTTAAAAGGTTTG TGCTACAAAGT[T/G]AA AGTGAATAAAGTGAAGA TTATCCACAGAGGAAAG AAAATATTTACAAATCAT GTATAT |
| 7 | ASGA0036855 | 126085856 | CC | [T/C] | TAGCAGATTTT GCCTTATCTAC CCAATTGCCT GTAAGCTGAG GGATGGCA | TATATATTCATTCTTACAC GAGGCATTATCGGACTA ACAGAGTGAAAAGCAAT TGAGTAC[T/C]TGCCATC CCTCAGCTTACAGGCA ATTGGGTAGATAAGGC AAAATCTGCTACGATGA GTAT |
| 5th segment | 18 | ALGA0097277 | 19527294 | GG | [A/G] | ATCAATGGGT TGAATATCTAA CAGGCATGTT TCTCTGTGTC CTCCAGTCT | GTTCCTCATTTGTTTTTC TGAGTAAATGAAAGCTT CCTAGACCTCCTGCCAG GCACCAGG[A/G]AGACT GGAGGACACAGAGAA ACATGCCTGTTAGATAT TCAACCCATTGATGGCC CTGGGG |
| | 18 | MARC0080197 | 19663776 | CC | [T/C] | ACAGCTGAAT GACAGTGTAC AATAATACAA ACACTTAAAC AATGAAAAGT | TTAATGTTCTTATCCTAG GTATAATTATCCCATATGT AAAATTTTTCACCTTTTT TTTTT[T/C]ACTTTTCAT TGTTTAAGTGTTTGTAT TATTGTACACTGTCATT CAGCTGTTCTCCTATAT |
| | 18 | H3GA0050489 | 19711697 | TT | [T/C] | GCAGCTGTAG CTCTGATTTG ACCCCTAACC CAGGAAGTTC CATATCCTGC | TAAGTCCAACATCTATAG TAACCAAAGAAATGCTT TTTTGTTTGTTTTGAGGG CCGAACW[T/C]GCAGGA TATGGAACTTCCTGGG TTAGGGGTCAAATCAG AGCTACAGCTGCTGGT CTATGA |

TABLE 1-continued

| chromosomename | SNP | the positions on the chromosomes | Genotype of Wuzhishan miniature pig inbred line | Source type of SNP | probe | Source sequence |
|---|---|---|---|---|---|---|
| 18 | ALGA0097281 | 19783081 | TT | [T/C] | CTTCTCAGGG CTTTTCCCTGT GTTCTTGACT TTCCACTGCC ATCTCTCAC | CTCAATCTCACTTCTCA GGGCTTTTCCCTGTGT TCTTGACTTTCCACTG CCATCTCTCAC[T/C]AC TGCTCTTTCCTTGTTCTT GACACAGCTGTCTCCCA TCCTTCCTGGGGAAGTA ATTCCC |
| 18 | H3GA0050490 | 19806130 | CC | [T/C] | GCCCAGGTCC CATTGTCACC CGAACTCGGA GCTGGGACTC TTCCAGTCCT | TTCGGGTCACTGGGCGG GTTCTGGTGGTGGGCT AGCGGCCTCAGGCTCAG GACGGTCAA[T/C]AGGA CTGGAAGAGTCCCAGC TCCGAGTTCGGGTGAC AATGGGACCTGGGCTC CTTTCAGC |
| 18 | ALGA0097282 | 19883611 | TT | [T/C] | CCCAACTGGC CTGGCTGAAA TGATAAGGGT GACTTCCTAC CTTACTCTTA | ACCAGAAGATCCCAAC TGGCCTGGCTGAAATG ATAAGGGTGACTTCCT ACCTTACTCTTA[T/C]G GACTGAATTGGCCCCAG CTCCAAATCCACATGTT GAAGGCCTAACCCCCAG TACGTCAG |
| 18 | ASGA0079089 | 19925205 | CC | [T/C] | TCTACCTGCA ACCTCTTCCTA CTCTAAACTCT AATAGCACTTT ATGCAGA | AAACCCTCTCTCTACCT GCAACCTCTTCCTACT CTAAACTCTAATAGCAC TTTATGCAGA[T/C]TTTT TTTGCATTTACTCCTTAA TGTACAGAGCTCATGTT CTTTTGCTAAACTTTAAG CTT |
| 18 | INRA0055354 | 19972451 | GG | [A/G] | GGAATGAGCT GCTACCTGGG GACACAGCTA GCCTGAGTGA TTTTATCATC | CAGCTAGCAGATTCAGC CTAGCCTATAGCAGCGTA AATCTTCAGGTAAAAATA TATTAGT[A/G]GATGATA AAATCACTCAGGCTAG CTGTGTCCCCAGGTAG CAGCTCATTCCTGAGC AGATT |
| 18 | ASGA0079091 | 20017978 | TT | [T/C] | CCTGTGCACT CTCTTCCCCAT TAGCGCAGAA AAGACCATCC ATCACCAGC | GGTTAGAGCAGTCTTCC TGTGCGCTCGCTCGGAG GCTTGTAGCTGTGACAT CACCATCCC[T/C]GCTG GTGATGGATGGTCTTT TCTGCGCTAATGGGGA AGAGAGTGCACAGGGC CGTCTGGG |
| 18 | ASGA0079090 | 20060777 | CC | [T/C] | TTCACCCACT GTATTGAGAA AGTACCAATA CCAACACAAA GAGCTTCGTG | GTGGGTGAACTTCAGAT GTCCTATCCACGAAGCT CTTTGTGTTGGTATCAGA TGTCCTAT[T/C]CACGAA GCTCTTTGTGTTGGTA TTGGTACTTTCTCAATA CAGTGGGTGAACTTCA GATGT |
| 18 | H3GA0050491 | 20112057 | AA | [A/G] | TTCAAGCCGC AGTTGTGACC TACGCTGCAG CTGTGGCAAT GCCGGATCCT | TGGGATTGGCAGTGTCT CTGGAGCACTGGGACGC AGGTTCGATCCCTGGCC TGTGTGGTT[A/G]AGGA TCCGGCATTGCCACAG CTGCAGCGTAGGTCAC AACTGCGGCTTGAATC AGATCCCT |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| 18 | MARC0056017 | 20126280 | TT | [T/C] | ACTAATTCCTT AGCCAGAGAC ATAAACAGGC ACAGAGCTGT AGTTGCCCT | ATCCCTAAGAACTAATT CCTTAGCCAGAGACAT AAACAGGCACAGAGCT GTAGTTGCCCT[T/C]CG CTCTGTGAGACACACAG CTGGCATGGAGGCTGAA TAAGGTCCCCRGATSTCA TGCTCC |
| 18 | MARC0055759 | 20304323 | AA | [A/C] | GGAGCTTTCT CTGCAAGCTT CCTGGTCACC CATCACTGCT TGAGGACACA | CTGGTACTCTGGAGCTT TCTCTGCAAGCTTCCT GGTCACCCATCACTGC TTGAGGACACA[A/C]AA AAGAACAATGGTACAG AGATGTGTCCCTGAAAA TTAGGATTTTTGTGTAGT CTTTTG |
| 18 | H3GA0050495 | 20338092 | GG | [A/G] | GAAGAATATG TAAGCATAAA TTTAAAGGCC CCTAGAGGAA GACAATATAT | AAAAGAACAGGAAGAA TATGTAAGCATAAATTT AAAGGCCCCTAGAGGA AGACAATATAT[A/G]TTT TAACACTTCCATACTCAG TTTCTTTAATTAAAAGA AAAGACTGAAAATCAAA ACTC |
| 18 | ALGA0097291 | 20376074 | GG | [A/G] | CAACTCCAAA TATAACAACTT TAATGGTCCTC ACTTAGCTTTA GGATTCC | ATTTTTAATTCAACTCCA AATATAACAACTTTAAT GGTCCTCACTTAGCTT TAGGATTCC[A/G]AATG GGAAAGGAATGACATAC ATACATACAATATTATTTC AGGGTTTTTTTCTACCC CC |
| 18 | ALGA0097290 | 20404568 | GG | [T/G] | CGGAGGCATA GCTTTGATCC CCAGCTCCGT GCAGTGTGTT ACAGGATCTG | CAGGTCGCTGCGGAGG CATAGCTTTGATCCCC AGCTCCGTGCAGTGTG TTACAGGATCTG[T/G]C ATTGCTATAGCTGTGGTG TAGGTTGCAGCTGTGGC TTGGATTCAATCCAAGG TGCAGGA |
| 18 | CASI0006683 | 20450764 | GG | [A/G] | GACAGTTTCT AACCAAACTA GAGTAGCAAA ATTTGAGTTC AAGTTGTAGT | AGCAGGTGGAGACAGT TTCTAACCAAACTAGA GTAGCAAAATTTGAGT TCAAGTTGTAGT[A/G]G AAAATTAAACTATCTTTT TAGATCCTTACCTTGAAA TATTTAGTTAACTAGATA GGACG |
| 18 | ASGA0079098 | 20520014 | CC | [T/C] | CATGAGTGGG CAAGAACACA CAGCTTGTTC CTGAGGTGAT GACTGGAAGC | GCAAGAGGTCCCAGAG AGGGGCCCAGGATTGCC CATCTACACTCCCCGGC AGGGGACACT[T/C]GCT TCCAGTCATCACCTCA GGAACAAGCTGTGTGT TCTTGCCCACTCATGAT CAATGTGC |
| 18 | ALGA0097297 | 20545597 | GG | [A/G] | GCCTTTGAGT TTAGGAGCCA GCTATATGGA AAAATCTAAA TGTCTCAGCA | CCCGCAACCTCACAGTT ACCAGTCAGATTCATTTC CGATGCACCACAACAGG AACTCCTC[A/G]TGCTG AGACATTTAGATTTTTC CATATAGCTGGCTCCTA AACTCAAAGGCACCTT GTTGA |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | 18 | H3GA0054426 | 20806040 | TT | [T/C] | GGAGGGAGG GATCAGGACC TAAGTAGGGC CATTCTGGAC AAGTGGGCAA A | GTAGGGAACAGGAGGG AGGGATCAGGACCTAA GTAGGGCCATTCTGGA CAAGTGGGCAAA[T/C]G TTGTCCAGGGCAAGTGG GAAGCCCGGAGNNNNN NNNNNNNNNNNNNNNN NNNNNNNNNN |
| 14th segment | 18 | ALGA0098112 | 43103162 | GG | [A/G] | TCAAACATCC TTATTTTCTTT TCTATTTTCT CTCCTATACTC TAGCCGG | GCAGCTGGGAGGCCTGA GGCATAAGTTGGCAGAG GTGATGGAAAGGGATGG AAGCTRGAA[A/G]CCGG CTAGAGTATAGGAGAG AAAAATAGAAAAGAAA ATAAGGATGTTTGAATC CCATCAG |
| | 18 | MARC0089391 | 43127872 | GG | [A/G] | TCTGGCAGCC GGCTATAGAG GGATAGGAGG GCAAGGAGCT CAATGGTCTG | TCTTCTTCCCATTGTCTC AGCTRTTGCCCTGGTGG AGCCCATCTTCATCTCTA GCAGCCC[A/G]CAGACC ATTGAGCTCCTTGCCC TCCTATCCCTCTATAGC CGGCTGCCAGAACGAA TT |
| | 18 | ASGA0089892 | 43229113 | AA | [A/G] | TGGAGGTGAT AGTCCAGCCA AGCATTGAAG GACGGAAGG GGGTTAGGAC A | GGCTTCTCTGTGGAGGT GATAGTCCAGCCAAGC ATTGAAGGACGGAAGG GGGTTAGGACA[A/G]GA GNNNNNNNNNNNNNNN NNNNNNNNNNNNNNNN NNNNNNNNNNNNNNNN NNNNNNNNN |
| | 18 | ASGA0097792 | 43232145 | CC | [T/C] | GGGGCCTCTA AGCCACCTGT CACTCATCCT CTTTCCTGGC CCAGAGGTTT | NNNNNNNNNNNNNNNN NNNNNNNNNNNNNNNN NNNNNNCTGTGAACAA CCACAAGAGACC[T/C]A AACCTCTGGGCCAGGA AAGAGGATGAGTGACA GGTGGCTTAGAGGCCC CAAGCAGTCGA |
| | 18 | MARC0046857 | 43251114 | GG | [A/G] | GAGTAAAGGG CTTTGAAGGA GAAGATTACT GTTCTCTCTTT GAAATGTTT | ATTATCTCTATGTACATAT CAAAAAAATCAGAGAA AAATGAACAATCTAGGT TATCATTA[A/G]AAACAT TTCAAAGAGAACAG TAATCTTCTCCTTCAAA GCCCTTTACTCACAATT CTTC |
| | 18 | MARC0077194 | 43266873 | AA | [A/G] | AACTCAGGAA AGTGTAACCC AGGTGTCCTC AAAGAGAAG GGGGGAGATT G | AGTGACCTGGAACTCA GGAAAGTGTAACCCAG GTGTCCTCAAAGAGAA GGGGGGAGATTG[A/G] TTATATAAAAATAACAAA AATAAAAACAAAAAATA AACAAAAACACAGGA AACTGCTTG |
| | 18 | ALGA0108769 | 43277580 | CC | [T/C] | GAGGCATGCT GTAGTATCTTT CAGCCATTAC CTGGGAGCAG GTTACTGAG | AGACACGGAGGAGGCA TGCTGTAGTATCTTTCA GCCATTACCTGGGAGC AGGTTACTGAG[T/C]CT TGGTTCAGTAAAGNNNN NNNNNNNNNNNNNNNN NNNNNNNNNNNNNNNN NNNNNNNNN |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | 18 | H3GA0050799 | 43325649 | CC | [T/C] | GCAGGATATA AACAGATATAT AGATGTAATC AAGCTTCCTC CTCCACCAA | CTGGAAAATGGCAGGAT ATAAACAGATATATAGA TGTAATCAAGCTTCCT CCTCCACCAA[T/C]GAA AACAGATCTTCTGCATG GCCGAACTCCACCTTGC CTCCTCAGAGGCCCTTT CACTTC |
| | 18 | ALGA0098120 | 43337188 | CC | [T/C] | CCTGGAAGTG GGCCAGACTG TAGATAAAGC GTTTGATGTG TCAGCAGTAG | TGCCATTTTTATCAAAGT TCAACCTTTCATCATCAT GTAAGTAGTCAAAGCTG TTACAAG[T/C]CTACTGC TGACACATCAAACGCT TTATCTACAGTCTGGC CCACTTCCAGGGAGAT GAAAA |
| | 18 | ALGA0098123 | 43370488 | GG | [A/G] | CCCAACACAG TGTCATGAGG ATGTGGGTTC AATCCCTGCC CTCACTCAGT | AGGTTAAGAACCCAAC ACAGTGTCATGAGGAT GTGGGTTCAATCCCTG CCCTCACTCAGT[A/G]G GTTGKGGATCTGGTGTT GCCGCAAGCTGGCAGTA CAGGTTGTAGATGTGGC TCAGATCC |
| | 18 | ALGA0098128 | 43394468 | GG | [A/G] | CTTTGTTTTAG GAGGGAGTCC TCAGCCAAGT CTAGCTAGAT GGGGATAGT | CATGATCAATGACAGAT GCCAGTCCTGAATTACC AAGGAGAATACCCCAGG GCTGCCCTT[A/G]ACTAT CCCCATCTAGCTAGAC TTGGCTGAGGACTCCC TCCTAAAACAAAGAATA ATGCAT |
| | 18 | ASGA0079719 | 43493743 | CC | [T/C] | CCTCTAGAAA CCTTGAAGGC TCTTGCATTCT TTCTTGGAGC CCAGCTTCC | CCTTAGTTCTCTTCCACA TGGCCTCTCATTCTCCAC TAGACTCCACTGGGCTT CTTTACA[T/C]GGAAGC TGGGCTCCAAGAAAGA ATGCAAGAGCCTTCAA GGTTTCTAGAGGCCCA GGCACA |
| | 18 | ASGA0079728 | 43556022 | GG | [A/G] | GTCTTATCAAA TGTGACCTGC TTCTGGCCAT GCAGGGTGGG AAGAATGTG | GGTCGAACTCAAGCAGA AGGTCCAAGATGTGAAC ACCAAGCTGTCCTACCC CCAGGGCTG[A/G]CACA TTCTTCCCACCCTGCA TGGCCAGAAGCAGGTC ACATTTGATAAGACTTT TCTTTAA |
| 20th segment | 18 | ASGA0080429 | 58958866 | CC | [T/C] | GATTTAGGAA AGCACTGAGT ATCAGCCATC CAGCCAAGGT AGGTACAGGA | GGAAAGGAAGGATTTA GGAAAGCACTGAGTAT CAGCCATCCAGCCAAG GTAGGTACAGGA[T/C]G GCATTCAAGCACAGAGT CCCCAGGAAGAGCTGCA GTCCTGATGCCCCATGCT GACACTG |
| | 18 | MARC0052755 | 59086075 | GG | [A/G] | TTCTCATACAC CATCCAATAA ACACTGACCA CATCCTGACC AGAGCTAAG | GAGAGCCAATTCTCAT ACACCATCCAATAAAC ACTGACCACATCCTGA CCAGAGCTAAG[A/G]AC TGTATAATGCTAAGCATA TCTAGG |
| | 18 | ALGA0098918 | 59451170 | GG | [A/G] | TCTGCATGTAA TTTAGTGCAG AGTGCCAGAA | GGAGTCTGAT**TCTGCAT GTAATTTAGTGCAGAG TGCCAGAATCCCGAGT |

TABLE 1-continued

| SNP chromosome | name | the positions on the chromosomes | Genotype of Wuzhishan miniature pig inbred line | Source type of SNP | probe | Source sequence |
|---|---|---|---|---|---|---|
| | | | | | TCCCGAGTAG CTGGGTTCC | AGCTGGGTTCC[A/G]GT CCTGGCTTGCCATTTACT AGGTACGTAACCCTGGG CACATTGCTGACCTGAT CCGTGC |
| 18 | ASGA0080432 | 59520434 | GG | [A/G] | GGAAGCCATT TTCCTCCTCCC GTGGACACAA TGAATGTGCA GCTACACAC | TGATGACACAGGAAGC CATTTTCCTCCTCCCGT GGACACAATGAATGTG CAGCTACACAC[A/G]RA GCAGTTCTCGCCGACAG AAATCTGGACGCCGAGA AAAGAGAGACATTCAGT TGAATGA |
| 18 | ALGA0098922 | 59553266 | CC | [T/C] | AAATTTTAAG TTAAAACAAG CTGTGCCCAG AGGAACATAT AGTCTGGCTC | GAGAAAAAAAAAATTT TAAGTTAAAACAAGCT GTGCCCAGAGGAACAT ATAGTCTGGCTC[T/C]T CAATGTCACAAGAAAAA TATGGGAAAGCTGAGCT TAGAGCTAAAAAGAACT ACTGATAT |
| 18 | INRA0056206 | 59600842 | GG | [A/G] | AACCGAAATT GTGTTTTCATC CCTGAGTTTC CAACTGTTCTA TTTAAGCA | AGCCAGATGCAACCGA AATTGTGTTTTCATCCC TGAGTTTCCAACTGTT CTATTTAAGCA[A/G]AA TTTTCTCTATTAAATTT GACTTTAAAATTTTAGA GACACATTTTTATCTTTT ACATT |
| 18 | INRA0056207 | 59625294 | CC | [T/C] | TAATCCTGAA AATAGCCGGG AAAATTCTTG AAAGAGAAG GACAGTTTGG G | ATCTATGTATCTTGGACC AAAATGGTTTTAGTTACT AAAATTCTGTTTTAACAT ACAATA[T/C]CCCAAAC TGTCCTTCTCTTTCAA GAATTTTCCCGGCTATT TTCAGGATTATCCCTCC AGA |
| 18 | ASGA0080435 | 59655603 | CC | [T/C] | GATATATTTAC ATGTGGGACT GAGTCACTCG GCTGCACACC TGAAGCTAA | ACAAAGAGTGGATATAT TTACATGTGGGACTGA GTCACTCGGCTGCACA CCTGAAGCTAA[T/C]GC AACATTATATATACATCA ACTATACTCAAATAAAAC TAATTTAAAAAGAAAA TTAAA |
| 18 | MARC0068495 | 59713388 | GG | [A/G] | AAATCTAGAG GTGGGAAACT TTGAGACAGC CTATTCCATTA GACTTGGGA | CTGTAACAGTTCAGGCA ACTGTCTCCCAGGGTTT TGCTAAGACACTGGGCG AACCTACAG[A/G]TCCC AAGTCTAATGGAATAG GCTGTCTCAAAGTTTC CCACCTCTAGATTTATA CAGGCAC |
| 18 | ASGA0080436 | 59739721 | CC | [T/C] | TTAATCAACTT CAGACATTTC CTCTTTGCCTC CTGCTTTGAC GAAAAGGC | GCACATGACTAAAATGC CGAGGGAGGGAAGCGA ACTGAGCCGAGCTATCA AAGTGCTGAA[T/C]GCC TTTTCGTCAAAGCAGG AGGCAAAGAGGAAATG TCTGAAGTTGATTAATG AGATACGA |
| 18 | MARC0003370 | 59753551 | CC | [T/C] | CCTTCCATTG GCTCTAGAAT AAGCTCCGGA TTGTACAAAT | CCCTGCACTACCTTCCA TTGGCTCTAGAATAAG CTCCGGATTGTACAAA TCTGACTCGGT[T/C]GT |

TABLE 1-continued

| chromosome | SNP name | the positions on the chromosomes | Genotype of Wuzhishan miniature pig inbred line | Source type of SNP | probe | Source sequence |
|---|---|---|---|---|---|---|
| | | | | | CTGACTCGGT | ACCCTGTTTAAAATCCTT CAGTAGCTT |
| 18 | ASGA0085659 | 59827202 | CC | [T/C] | AGTTGGTTTC GTTGCTGCTG AGCCACAACA GGAATTCATAT TAAGAACAT | CATGGATTCCAGTTGGT TTCGTTGCTGCTGAGC CACAACAGGAATTCAT ATTAAGAACAT[T/C]TTT AAGYGATACTAGNNNNN NNNNNNNNNNNNNNNN NNNNNNNNNNNNNNNN NNNNNNNN |

In table 1, N represents A, T, C, or G. In table 1, underlines in source sequence label the regions to which probes correspond (containing two cases, the nucleotide sequence of probe is same as that of underline region, the nucleotide sequence of probe is reversely complementary to that of underline region). In table 1, when source type of SNP is [T/G], heterozygous type is TG; when source type of SNP is [A/G], heterozygous type is AG; when source type of SNP is [T/C], heterozygous type is TC; and when source type of SNP is [A/C], heterozygous type is AC.

Example 2. Identifying Wuzhishan Miniature Pig Inbred Line and Non-Wuzhishan Miniature Pig Inbred Line by Using 145 SNPs 1. Selecting experimental animals, collecting blood from ear veins, and extracting genomic DNA from blood samples;

2. Hybridizing the genomic DNA obtained in Step 1 with nucleic acid chips immobilized with 145 probes (these 145 probes are single-stranded DNA molecules shown as Sequences 1-145 in the sequence listing, respectively);

3. After accomplishing Step 2, terminal extensions were performed on each point in nucleic acid chips, so as to obtain the genotypes of 145 SNP sites in genomic DNA;

4. Whole genome sequencing was performed on genomic DNA obtained in Step 1 to obtain the genotypes of 145 SNP sites in genomic DNA.

The results demonstrated that the results of Step 3 are completely consistent with those of Step 4.

Genotypes of 145 SNP sites of 48 experimental animals of Wuzhishan miniature pig inbred line are all homozygous type (genotypes described in Table 1 of Example 1). Genotypes of 145 SNP sites of 16 experimental animals of Hainan Wuzhishan pig are all heterozygous type.

INDUSTRIAL APPLICATION

The present invention is of a significant value for the identification of germplasm resource of Wuzhishan miniature pig inbred line. The method of the present invention can be used for breeding of Wuzhishan miniature pig inbred line, preliminarily screening all the pigs in the pig population to be tested, weeding out non-Wuzhishan miniature pig inbred line, finding out candidate Wuzhishan miniature pig inbred line, and further confirming in combination with other methods. The present invention also can be applied to test whether the purchased Wuzhishan miniature pig inbred line is counterfeit.

The invention claimed is:

1. A method for auxiliarily identifying whether a pig is Wuzhishan miniature pig inbred line, comprising:
   a) obtaining a DNA sample from the pig;
   b) testing a genotype of the pig by hybridizing the DNA sample with each of 145 probes and terminally extending each of the hybridized 145 probes; and
   c) identifying the pig to be a candidate for Wuzhishan miniature pig inbred line based on 145 SNP sites if all standards of the following (1) to (145) are satisfied
   (1) M1GA0025062 the genotype of SNP site is GG;
   (2) DRGA0017627 the genotype of SNP site is GG;
   (3) H3GA0056137 the genotype of SNP site is CC;
   (4) MARC0039661 the genotype of SNP site is AA;
   (5) ASGA0085025 the genotype of SNP site is TT;
   (6) ASGA0098570 the genotype of SNP site is GG;
   (7) MARC0063358 the genotype of SNP site is AA;
   (8) ASGA0085437 the genotype of SNP site is GG;
   (9) MARC0096709 the genotype of SNP site is CC;
   (10) H3GA0052387 the genotype of SNP site is GG;
   (11) ASGA0000264 the genotype of SNP site is TT;
   (12) ALGA0000195 the genotype of SNP site is TT;
   (13) H3GA0001444 the genotype of SNP site is AA;
   (14) ASGA0002293 the genotype of SNP site is CC;
   (15) INRA0001752 the genotype of SNP site is GG;
   (16) H3GA0001445 the genotype of SNP site is GG;
   (17) ALGA0002595 the genotype of SNP site is TT;
   (18) ALGA0002600 the genotype of SNP site is GG;
   (19) DRGA0000563 the genotype of SNP site is CC;
   (20) DRGA0000565 the genotype of SNP site is CC;
   (21) INRA0001761 the genotype of SNP site is AA;
   (22) MARC0104045 the genotype of SNP site is CC;
   (23) ALGA0002601 the genotype of SNP site is CC;
   (24) DRGA0000569 the genotype of SNP site is AA;

(25) ALGA0002608 the genotype of SNP site is TT;
(26) DRGA0000568 the genotype of SNP site is CC;
(27) ALGA0002604 the genotype of SNP site is GG;
(28) MARC0048118 the genotype of SNP site is TT;
(29) ASGA0004229 the genotype of SNP site is CC;
(30) MARC0007088 the genotype of SNP site is CC;
(31) MARC0000061 the genotype of SNP site is GG;
(32) MARC0094747 the genotype of SNP site is AA;
(33) MARC0007969 the genotype of SNP site is AA;
(34) ASGA0106092 the genotype of SNP site is CC;
(35) ALGA0119806 the genotype of SNP site is GG;
(36) INRA0003745 the genotype of SNP site is AA;
(37) INRA0003746 the genotype of SNP site is TT;
(38) ALGA0005490 the genotype of SNP site is CC;
(39) H3GA0002538 the genotype of SNP site is CC;
(40) INRA0003749 the genotype of SNP site is CC;
(41) H3GA0002539 the genotype of SNP site is GG;
(42) M1GA0001099 the genotype of SNP site is CC;
(43) MARC0111831 the genotype of SNP site is AA;
(44) ASGA0005566 the genotype of SNP site is CC;
(45) ALGA0007578 the genotype of SNP site is CC;
(46) ASGA0005568 the genotype of SNP site is CC;
(47) INRA0005765 the genotype of SNP site is AA;
(48) MARC0095347 the genotype of SNP site is CC;
(49) MARC0039015 the genotype of SNP site is CC;
(50) DRGA0001892 the genotype of SNP site is GG;
(51) ALGA0007580 the genotype of SNP site is GG;
(52) ALGA0007583 the genotype of SNP site is TT;
(53) MARC0095915 the genotype of SNP site is CC;
(54) ASGA0005571 the genotype of SNP site is AA;
(55) MARC0014134 the genotype of SNP site is AA;
(56) MARC0024233 the genotype of SNP site is AA;
(57) H3GA0003548 the genotype of SNP site is GG;
(58) ALGA0007591 the genotype of SNP site is CC;
(59) MARC0000195 the genotype of SNP site is CC;
(60) ALGA0038697 the genotype of SNP site is CC;
(61) H3GA0020000 the genotype of SNP site is CC;
(62) ALGA0038703 the genotype of SNP site is CC;
(63) H3GA0020002 the genotype of SNP site is GG;
(64) DRGA0007138 the genotype of SNP site is CC;
(65) ASGA0031284 the genotype of SNP site is CC;
(66) ASGA0031285 the genotype of SNP site is AA;
(67) MARC0025042 the genotype of SNP site is GG;
(68) H3GA0020006 the genotype of SNP site is TT;
(69) ALGA0038729 the genotype of SNP site is CC;
(70) ALGA0038731 the genotype of SNP site is GG;
(71) ASGA0031321 the genotype of SNP site is GG;
(72) ASGA0031322 the genotype of SNP site is GG;
(73) ALGA0038747 the genotype of SNP site is AA;
(74) ASGA0033095 the genotype of SNP site is TT;
(75) ALGA0040854 the genotype of SNP site is GG;
(76) ALGA0040856 the genotype of SNP site is AA;
(77) ALGA0040857 the genotype of SNP site is GG;
(78) ASGA0033096 the genotype of SNP site is GG;
(79) INRA0025180 the genotype of SNP site is AA;
(80) ALGA0040859 the genotype of SNP site is CC;
(81) H3GA0021216 the genotype of SNP site is CC;
(82) ASGA0033098 the genotype of SNP site is CC;
(83) H3GA0021221 the genotype of SNP site is CC;
(84) MARC0014540 the genotype of SNP site is CC;
(85) ASGA0033103 the genotype of SNP site is CC;
(86) DIAS0000557 the genotype of SNP site is AA;
(87) ASGA0033116 the genotype of SNP site is AA;
(88) ASGA0036835 the genotype of SNP site is CC;
(89) MARC0031932 the genotype of SNP site is CC;
(90) ASGA0036838 the genotype of SNP site is CC;
(91) H3GA0023523 the genotype of SNP site is GG;
(92) ALGA0045460 the genotype of SNP site is TT;
(93) MARC0005927 the genotype of SNP site is GG;
(94) MARC0005928 the genotype of SNP site is AA;
(95) ASGA0036842 the genotype of SNP site is CC;
(96) ASGA0036846 the genotype of SNP site is CC;
(97) MARC0098637 the genotype of SNP site is TT;
(98) M1GA0011035 the genotype of SNP site is TT;
(99) DRGA0008230 the genotype of SNP site is GG;
(100) ASGA0036855 the genotype of SNP site is CC;
(101) ALGA0097277 the genotype of SNP site is GG;
(102) MARC0080197 the genotype of SNP site is CC;
(103) H3GA0050489 the genotype of SNP site is TT;
(104) ALGA0097281 the genotype of SNP site is TT;
(105) H3GA0050490 the genotype of SNP site is CC;
(106) ALGA0097282 the genotype of SNP site is TT;
(107) ASGA0079089 the genotype of SNP site is CC;
(108) INRA0055354 the genotype of SNP site is GG;
(109) ASGA0079091 the genotype of SNP site is TT;
(110) ASGA0079090 the genotype of SNP site is CC;
(111) H3GA0050491 the genotype of SNP site is AA;
(112) MARC0056017 the genotype of SNP site is TT;
(113) MARC0055759 the genotype of SNP site is AA;
(114) H3GA0050495 the genotype of SNP site is GG;
(115) ALGA0097291 the genotype of SNP site is GG;
(116) ALGA0097290 the genotype of SNP site is GG;
(117) CASI0006683 the genotype of SNP site is GG;
(118) ASGA0079098 the genotype of SNP site is CC;
(119) ALGA0097297 the genotype of SNP site is GG;
(120) H3GA0054426 the genotype of SNP site is TT;
(121) ALGA0098112 the genotype of SNP site is GG;
(122) MARC0089391 the genotype of SNP site is GG;
(123) ASGA0089892 the genotype of SNP site is AA;
(124) ASGA0097792 the genotype of SNP site is CC;
(125) MARC0046857 the genotype of SNP site is GG;
(126) MARC0077194 the genotype of SNP site is AA;
(127) ALGA0108769 the genotype of SNP site is CC;
(128) H3GA0050799 the genotype of SNP site is CC;
(129) ALGA0098120 the genotype of SNP site is CC;
(130) ALGA0098123 the genotype of SNP site is GG;
(131) ALGA0098128 the genotype of SNP site is GG;
(132) ASGA0079719 the genotype of SNP site is CC;
(133) ASGA0079728 the genotype of SNP site is GG;
(134) ASGA0080429 the genotype of SNP site is CC;
(135) MARC0052755 the genotype of SNP site is GG;
(136) ALGA0098918 the genotype of SNP site is GG;
(137) ASGA0080432 the genotype of SNP site is GG;
(138) ALGA0098922 the genotype of SNP site is CC;
(139) INRA0056206 the genotype of SNP site is GG;
(140) INRA0056207 the genotype of SNP site is CC;
(141) ASGA0080435 the genotype of SNP site is CC;
(142) MARC0068495 the genotype of SNP site is GG;
(143) ASGA0080436 the genotype of SNP site is CC;
(144) MARC0003370 the genotype of SNP site is CC;
(145) ASGA0085659 the genotype of SNP site is CC;
and, if any standard of the above (1) to (145) is not satisfied, the pig is a candidate for non-Wuzhishan miniature pig inbred line.

2. The method of claim 1, wherein the pig is Wuzhishan miniature pig inbred line or Hainan Wuzhishan pig.

3. The method of claim 1, wherein the Wuzhishan miniature pig inbred line belongs to any one of $F_{20}$ to $F_{22}$ generations.

4. The method of claim 1, wherein the Wuzhishan miniature pig inbred line belongs to $F_{20}$ generation or generations later than $F_{20}$ generation.

5. The method of claim 1, wherein the 145 probes are included in a chip and selected from SEQ ID NOs: 1-145.

6. The method of claim 5, wherein the 145 probes are immobilized at different points of the chip, respectively.

7. A nucleic acid chip, in which single-stranded DNA molecules shown as SEQ ID NOs: 1-145 are immobilized at different points, respectively.

8. A method for auxiliarily identifying whether a pig to be tested is Wuzhishan miniature pig inbred line or auxiliarily identifying whether a pig population to be tested is Wuzhishan miniature pig inbred line population, comprising:
- (a) obtaining a genomic DNA from the pig to be tested or from the pig population to be tested
- (b) hybridizing the genomic DNA with each of the single-stranded DNA molecules on each point in the nucleic acid chip of claim 7;
- (c) terminally extending the hybridized single-stranded DNA molecules on each point of the nucleic acid chip, to obtain genotypes of 145 SNP sites in the genomic DNA;
- (d) identifying whether the pig to be tested is Wuzhishan miniature pig inbred line or whether the pig population to be tested is Wuzhishan miniature pig inbred line population based on the genotypes of 145 SNP sites in the genomic DNA.

9. A method for auxiliarily identifying whether a pig population to be tested is Wuzhishan miniature pig inbred line population, comprising the following steps:
- i) randomly sampling from the pig population to be tested to obtain DNA samples to be tested,
- ii) testing genotypes of each of the DNA samples to be tested by hybridizing the DNA sample with each of 145 probes and terminally extending each of the hybridized 145 probes; and
- iii) the pig population to be tested is a candidate for a Wuzhishan miniature pig inbred line population based on 145 SNP sites if all the DNA samples to be tested satisfy all standards of the following (1) to (145):
  - (1) M1GA0025062 the genotype of SNP site is GG;
  - (2) DRGA0017627 the genotype of SNP site is GG;
  - (3) H3GA0056137 the genotype of SNP site is CC;
  - (4) MARC0039661 the genotype of SNP site is AA;
  - (5) ASGA0085025 the genotype of SNP site is TT;
  - (6) ASGA0098570 the genotype of SNP site is GG;
  - (7) MARC0063358 the genotype of SNP site is AA;
  - (8) ASGA0085437 the genotype of SNP site is GG;
  - (9) MARC0096709 the genotype of SNP site is CC;
  - (10) H3GA0052387 the genotype of SNP site is GG;
  - (11) ASGA0000264 the genotype of SNP site is TT;
  - (12) ALGA0000195 the genotype of SNP site is TT;
  - (13) H3GA0001444 the genotype of SNP site is AA;
  - (14) ASGA0002293 the genotype of SNP site is CC;
  - (15) INRA0001752 the genotype of SNP site is GG;
  - (16) H3GA0001445 the genotype of SNP site is GG;
  - (17) ALGA0002595 the genotype of SNP site is TT;
  - (18) ALGA0002600 the genotype of SNP site is GG;
  - (19) DRGA0000563 the genotype of SNP site is CC;
  - (20) DRGA0000565 the genotype of SNP site is CC;
  - (21) INRA0001761 the genotype of SNP site is AA;
  - (22) MARC0104045 the genotype of SNP site is CC;
  - (23) ALGA0002601 the genotype of SNP site is CC;
  - (24) DRGA0000569 the genotype of SNP site is AA;
  - (25) ALGA0002608 the genotype of SNP site is TT;
  - (26) DRGA0000568 the genotype of SNP site is CC;
  - (27) ALGA0002604 the genotype of SNP site is GG;
  - (28) MARC0048118 the genotype of SNP site is TT;
  - (29) ASGA0004229 the genotype of SNP site is CC;
  - (30) MARC0007088 the genotype of SNP site is CC;
  - (31) MARC0000061 the genotype of SNP site is GG;
  - (32) MARC0094747 the genotype of SNP site is AA;
  - (33) MARC0007969 the genotype of SNP site is AA;
  - (34) ASGA0106092 the genotype of SNP site is CC;
  - (35) ALGA0119806 the genotype of SNP site is GG;
  - (36) INRA0003745 the genotype of SNP site is AA;
  - (37) INRA0003746 the genotype of SNP site is TT;
  - (38) ALGA0005490 the genotype of SNP site is CC;
  - (39) H3GA0002538 the genotype of SNP site is CC;
  - (40) INRA0003749 the genotype of SNP site is CC;
  - (41) H3GA0002539 the genotype of SNP site is GG;
  - (42) M1GA0001099 the genotype of SNP site is CC;
  - (43) MARC0111831 the genotype of SNP site is AA;
  - (44) ASGA0005566 the genotype of SNP site is CC;
  - (45) ALGA0007578 the genotype of SNP site is CC;
  - (46) ASGA0005568 the genotype of SNP site is CC;
  - (47) INRA0005765 the genotype of SNP site is AA;
  - (48) MARC0095347 the genotype of SNP site is CC;
  - (49) MARC0039015 the genotype of SNP site is CC;
  - (50) DRGA0001892 the genotype of SNP site is GG;
  - (51) ALGA0007580 the genotype of SNP site is GG;
  - (52) ALGA0007583 the genotype of SNP site is TT;
  - (53) MARC0095915 the genotype of SNP site is CC;
  - (54) ASGA0005571 the genotype of SNP site is AA;
  - (55) MARC0014134 the genotype of SNP site is AA;
  - (56) MARC0024233 the genotype of SNP site is AA;
  - (57) H3GA0003548 the genotype of SNP site is GG;
  - (58) ALGA0007591 the genotype of SNP site is CC;
  - (59) MARC0000195 the genotype of SNP site is CC;
  - (60) ALGA0038697 the genotype of SNP site is CC;
  - (61) H3GA0020000 the genotype of SNP site is CC;
  - (62) ALGA0038703 the genotype of SNP site is CC;
  - (63) H3GA0020002 the genotype of SNP site is GG;
  - (64) DRGA0007138 the genotype of SNP site is CC;
  - (65) ASGA0031284 the genotype of SNP site is CC;
  - (66) ASGA0031285 the genotype of SNP site is AA;
  - (67) MARC0025042 the genotype of SNP site is GG;
  - (68) H3GA0020006 the genotype of SNP site is TT;
  - (69) ALGA0038729 the genotype of SNP site is CC;
  - (70) ALGA0038731 the genotype of SNP site is GG;
  - (71) ASGA0031321 the genotype of SNP site is GG;
  - (72) ASGA0031322 the genotype of SNP site is GG;
  - (73) ALGA0038747 the genotype of SNP site is AA;
  - (74) ASGA0033095 the genotype of SNP site is TT;
  - (75) ALGA0040854 the genotype of SNP site is GG;
  - (76) ALGA0040856 the genotype of SNP site is AA;
  - (77) ALGA0040857 the genotype of SNP site is GG;
  - (78) ASGA0033096 the genotype of SNP site is GG;
  - (79) INRA0025180 the genotype of SNP site is AA;
  - (80) ALGA0040859 the genotype of SNP site is CC;
  - (81) H3GA0021216 the genotype of SNP site is CC;
  - (82) ASGA0033098 the genotype of SNP site is CC;
  - (83) H3GA0021221 the genotype of SNP site is CC;
  - (84) MARC0014540 the genotype of SNP site is CC;
  - (85) ASGA0033103 the genotype of SNP site is CC;
  - (86) DIAS0000557 the genotype of SNP site is AA;
  - (87) ASGA0033116 the genotype of SNP site is AA;
  - (88) ASGA0036835 the genotype of SNP site is CC;
  - (89) MARC0031932 the genotype of SNP site is CC;
  - (90) ASGA0036838 the genotype of SNP site is CC;
  - (91) H3GA0023523 the genotype of SNP site is GG;
  - (92) ALGA0045460 the genotype of SNP site is TT;
  - (93) MARC0005927 the genotype of SNP site is GG;
  - (94) MARC0005928 the genotype of SNP site is AA;
  - (95) ASGA0036842 the genotype of SNP site is CC;
  - (96) ASGA0036846 the genotype of SNP site is CC;
  - (97) MARC0098637 the genotype of SNP site is TT;
  - (98) M1GA0011035 the genotype of SNP site is TT;

(99) DRGA0008230 the genotype of SNP site is GG;
(100) ASGA0036855 the genotype of SNP site is CC;
(101) ALGA0097277 the genotype of SNP site is GG;
(102) MARC0080197 the genotype of SNP site is CC;
(103) H3GA0050489 the genotype of SNP site is TT;
(104) ALGA0097281 the genotype of SNP site is TT;
(105) H3GA0050490 the genotype of SNP site is CC;
(106) ALGA0097282 the genotype of SNP site is TT;
(107) ASGA0079089 the genotype of SNP site is CC;
(108) INRA0055354 the genotype of SNP site is GG;
(109) ASGA0079091 the genotype of SNP site is TT;
(110) ASGA0079090 the genotype of SNP site is CC;
(111) H3GA0050491 the genotype of SNP site is AA;
(112) MARC0056017 the genotype of SNP site is TT;
(113) MARC0055759 the genotype of SNP site is AA;
(114) H3GA0050495 the genotype of SNP site is GG;
(115) ALGA0097291 the genotype of SNP site is GG;
(116) ALGA0097290 the genotype of SNP site is GG;
(117) CASI0006683 the genotype of SNP site is GG;
(118) ASGA0079098 the genotype of SNP site is CC;
(119) ALGA0097297 the genotype of SNP site is GG;
(120) H3GA0054426 the genotype of SNP site is TT;
(121) ALGA0098112 the genotype of SNP site is GG;
(122) MARC0089391 the genotype of SNP site is GG;
(123) ASGA0089892 the genotype of SNP site is AA;
(124) ASGA0097792 the genotype of SNP site is CC;
(125) MARC0046857 the genotype of SNP site is GG;
(126) MARC0077194 the genotype of SNP site is AA;
(127) ALGA0108769 the genotype of SNP site is CC;
(128) H3GA0050799 the genotype of SNP site is CC;
(129) ALGA0098120 the genotype of SNP site is CC;
(130) ALGA0098123 the genotype of SNP site is GG;
(131) ALGA0098128 the genotype of SNP site is GG;
(132) ASGA0079719 the genotype of SNP site is CC;
(133) ASGA0079728 the genotype of SNP site is GG;
(134) ASGA0080429 the genotype of SNP site is CC;
(135) MARC0052755 the genotype of SNP site is GG;
(136) ALGA0098918 the genotype of SNP site is GG;
(137) ASGA0080432 the genotype of SNP site is GG;
(138) ALGA0098922 the genotype of SNP site is CC;
(139) INRA0056206 the genotype of SNP site is GG;
(140) INRA0056207 the genotype of SNP site is CC;
(141) ASGA0080435 the genotype of SNP site is CC;
(142) MARC0068495 the genotype of SNP site is GG;
(143) ASGA0080436 the genotype of SNP site is CC;
(144) MARC0003370 the genotype of SNP site is CC;
(145) ASGA0085659 the genotype of SNP site is CC;
if more than one of the DNA samples to be tested does not satisfy all the standards of the above (1) to (145), the pig population to be tested is a candidate for non-Wuzhishan miniature pig inbred line population.

10. The method of claim 9, wherein the pig population to be tested is Wuzhishan miniature pig inbred line or Hainan Wuzhishan pig.

11. The method of claim 9, wherein the Wuzhishan miniature pig inbred line belongs to any one of $F_{20}$ to $F_{22}$ generations.

12. The method of claim 9, wherein the Wuzhishan miniature pig inbred line belongs to $F_{20}$ generation or generations later than $F_{20}$ generation.

13. The method of claim 9, wherein the 145 probes are included in a chip and selected from SEQ ID NOs: 1-145.

14. The method of claim 13, wherein the 145 probes are immobilized at different points of the chip, respectively.

* * * * *